(12) United States Patent
Omote et al.

(10) Patent No.: US 7,098,459 B2
(45) Date of Patent: Aug. 29, 2006

(54) METHOD OF PERFORMING ANALYSIS USING PROPAGATION RAYS AND APPARATUS FOR PERFORMING THE SAME

(75) Inventors: Kazuhiko Omote, Tokyo (JP); Akito Sasaki, Tokyo (JP); Yoshiyasu Ito, Tokyo (JP)

(73) Assignee: Rigaku Corporation, Akishima (JP)

( * ) Notice: Subject to any disclaimer, the term of this patent is extended or adjusted under 35 U.S.C. 154(b) by 125 days.

(21) Appl. No.: 10/457,464

(22) Filed: Jun. 10, 2003

(65) Prior Publication Data

US 2003/0231737 A1 Dec. 18, 2003

(30) Foreign Application Priority Data

Jun. 12, 2002 (JP) .............................. 2002-171110

(51) Int. Cl.
*G01F 23/00* (2006.01)
*G01N 23/20* (2006.01)
*G01N 23/201* (2006.01)

(52) U.S. Cl. .................. 250/358.1; 378/70; 378/86

(58) Field of Classification Search ............ 250/358.1, 250/306–307; 378/70, 86; 702/109, 85, 702/189, 198

See application file for complete search history.

(56) References Cited

U.S. PATENT DOCUMENTS 6,330,301 B1 12/2001 Jiang
2003/0157559 A1 8/2003 Omote et al.

FOREIGN PATENT DOCUMENTS

JP 2001-349849 12/2001
WO WO 01/75426 A1 10/2001

OTHER PUBLICATIONS

Luban, M. and Deutsch, M. "Exact Solution of the Slit-Height Correction Problem in Small-Angle X-ray Scattering. I. The General Method and its Accuracy in Application to Simulated Data". J. Appl Cryst., vol. 11, pt. 2 (Apr. 1, 1978), pp. 87-97.*
Luban, M. and Deutsch, M. "Exact Solution of the Slit-Height Correction Problem in Small-Angle X-ray Scattering. II. A Method for Arbitrary Slit Transmission Functions". Journal of Applied Crystallography. vol. 11, pt. 2 (Apr. 1, 1978), pp. 98-101.*

(Continued)

*Primary Examiner*—David Porta
*Assistant Examiner*—Frederick F. Rosenberger
(74) *Attorney, Agent, or Firm*—Buchanan Ingersoll PC

(57) ABSTRACT

Disclosed herein is a sample-analyzing method, in which an incident beam slit is provided between an X-ray source and a sample, a receiving side beam slit is provided between the sample and an X-ray detector, the X-ray detector detects X-rays scattered again from the sample and coming through the receiving side beam slit when the sample is irradiated with the X-rays applied through the incident beam slit, and a value is measured from a value detected by the X-ray detector. In the method, a true value is measured from the value, by using a slit function representing an influence which the incident beam slit and receiving side beam slit impose on the detected value. The slit function is determined from an intensity distribution of the X-rays scattered again from the sample. The method obtains an accurate slit function in accordance with the structure of the optical system employed and can therefore analyze the sample with high precision.

21 Claims, 28 Drawing Sheets

OTHER PUBLICATIONS

Luban, M. and Deutsch, M. "Exact Solution of the Slit-Height Correction Problem in Small-Angle X-ray Scattering. III. Derivation of Slit Correction Functions". Journal of Applied Crystallography. vol. 13, No. 3 (Jun. 1, 1980), pp. 233-243.*

D. Balzar et al, "Synchrotron X-Ray Diffraction Line Profile", FIZIKA A, vol. 6, 1997, pp. 41-50.

M.S. Dixit et al., "Development of Gas Microstrip Detectors for Digital X-Ray Imaging and Radiation Dosimetry", IEEE Instrumentation and Measurement Technology Conference, Ottawa, Canada, May 19-21, 1997, pp. 1357-1360, IEEE, NY, NY, USA.

J.C. Yanch et al, "Monte Carlo Simulation in SPECT: Complete 3D Modelling of Source, Collimator and Tomographic Data Acquisition", Proceedings of the Nuclear Science Symposium and Medical Imaging Conference, Santa Fe, Nov. 2-9, 1991, vol. 1, Nov. 2, 1991, pp. 1809-1813, IEEE, NY, USA.

V. Veretennikov, "Effect of the Instrumental Function on Measurements of Phase Functions of Scattering by Large Particles at Small Scattering Angles", Proceedings of 1998 5th International Symposium on Atmospheric and Ocean Optics; Jun. 15-18, 1998, Proceedings of SPIE vol. 3583, 1999, pp. 182-189, SPIE—The International Society for Optical Engineering Society, Bellingham, WA, USA.

* cited by examiner

SCATTERING ANGLE OF VERTICAL COMPONENTS AND X-RAY INTENSITY DISTRIBUTION, WHEN VERTICAL ANGLE OF INCIDENT X-RAYS = 0°, AND X-RAY IRRADIATION POSITION (Y) = 0

SCATTERING ANGLE OF VERTICAL COMPONENTS AND X-RAY INTENSITY DISTRIBUTION, WHEN VERTICAL ANGLE OF INCIDENT X-RAYS = $\theta_{N\text{-}in}^{min}$ AND X-RAY IRRADIATION POSITION (Y) = 0

CONVOLUTION AT THE INCIDENT SIDE AND RECEIVING SIDE

CONVOLUTION AT THE INCIDENT SIDE AND RECEIVING SIDE

METHOD OF PERFORMING ANALYSIS USING PROPAGATION RAYS AND APPARATUS FOR PERFORMING THE SAME

BACKGROUND OF THE INVENTION

1. Field of the Invention

The present invention relates to a method and an apparatus, both designed to analyze a sample by applying propagation rays, such as X-rays and particle beams, to the sample.

2. Description of the Related Art

A method of analyzing a sample by applying propagation rays, such as X-rays, to the sample is disclosed in, for example, Japanese Unexamined Patent Publication No. 2001-349849. In the method disclosed in the publication, an X-ray scattering curve simulated of a thin film is compared with an X-ray scattering curve measured of the thin film, in order to evaluate the non-uniformity of density of the particles contained in the thin film.

To simulate the X-ray scattering curve, a scattering function $I(q)$ is set in advance. The scattering function $I(q)$ includes one or more fitting parameters selected from parameters pertaining to the scattering state of particles. Among these parameters are average particle size parameter "R0," distribution-broadening parameter "M," diameter parameter "D," aspect-ratio parameter "a," minimum inter-particle distance parameter "L," inter-particle correlation coefficient parameter "$\eta$," particle-content parameter "P," inter-particle distance parameter "$\epsilon$", and the like.

The simulated X-ray scattering curve may coincide with the X-ray scattering curve actually obtained. In this case, it is determined that the values of the fitting parameters simulating the X-ray scattering curve represent the scattering state of the particles in the thin film.

This method can analyze thin films in non-destructive fashion, more easily, more quickly and more precisely than the gas adsorption and the small angle X-ray scattering, both hitherto known.

Japanese Unexamined Patent Publication No. 2001-349849 describes in, for example, paragraph [0086] that the scattering function actually acquired can be effectively corrected by using a slit function, in order to correct the error that has resulted from the limited length of the slit. However, the slit function disclosed in Japanese Unexamined Patent Publication No. 2001-349849 is very simple. Due to this, the slit correction may not be accomplished as precisely as desired in the optical system employed in practice.

SUMMARY OF THE INVENTION

The present invention has been made in view of the foregoing. An object of the invention is to provide a method and apparatus that can analyze a sample with high precision, by obtaining a correct slit function that is desirable for the optical system actually employed.

To attain the object, a sample-analyzing method according to this invention comprises: (a) providing an incident beam slit between a propagation-ray source and a sample; (b) providing a receiving side beam slit between the sample and detecting means; (c) causing the detecting means to detect propagation rays re-generated from the sample and coming through the receiving side beam slit when the sample is irradiated with the propagation rays applied through the incident beam slit; (d) measuring a value from a value detected by the detecting means; and (e) calculating a true value from the value measured, by using a slit function representing an influence which the incident beam slit and receiving side beam slit impose on the value detected by the detecting means. (f) In the method, the slit function is determined from an intensity distribution of the propagation rays scattered again from the sample.

The above-mentioned slit function is a function that represents the influence that the sizes and positions of the incident beam slit and the receiving side beam slit impose on the intensity and resolution of the propagation rays, such as X-rays.

In the analyzing method described above, the slit function is determined from the intensity distribution of the propagation rays, e.g., X-rays, scattered again from the sample. The slit function is therefore pertains to the slits used in the optical system. This helps to analyze the sample correctly.

In the analyzing method designed as described above, the propagation rays are those that can propagate in space. They may be X-rays or particle beams. The particle beams may be neutron beams or electron beams.

In the analyzing method designed as specified above, it is desirable to determine the slit function from a variable that represents a position in a lengthwise direction of the sample, where the sample is irradiated with the propagation rays. Then, the slit function can be an accurate one more pertaining to the optical system than otherwise. The sample can therefore be analyzed with a higher precision.

In the analyzing method designed as explained above, it is desirable to determine the slit function on the basis of the fact that an angle formed by lines of sight which extends from the sample to the propagation-ray source through the incident beam slit and an angle formed by lines of sight which extends from the sample to the detecting means through the receiving side beam slit change in accordance with a position in a lengthwise direction of the sample. In this case, too, the slit function can be an accurate one more pertaining to the optical system than otherwise. The sample can therefore be analyzed with a higher precision.

In the analyzing method designed as explained above, it is desirable to determine the slit function from a convolution of two intensity distributions that the propagation rays assume at an incident side and receiving side of the sample, respectively. If so, the slit function can be an accurate one more pertaining to the optical system than otherwise. The sample can therefore be analyzed with a higher precision.

In the method described above, the slit function used in the optical system represents the influence that the sizes and positions of the incident beam slit and receiving side beam slit impose on the intensity and resolution of X-rays. How the slit function is obtained will be explained below.

(A) Generally, X-ray diffraction profiles depend on the scattering angle $2\theta$. Any regions that have the same scattering angle $2\theta$ extend from the sample S like a cone as illustrated in FIG. 4. The rings D, or the circumferences of the bases of the cones, are generally known as "Debye rings." The Debye rings D may be measured by using a rectangular slit that has a limited height and extends vertically, or in a direction perpendicular to the scattering plane. Then, an umbrella effect will be observed as seen from FIG. 5.

The umbrella effect is a change in the measuring results, which is caused by the Debye rings D moves, gradually expanding, thus defining cones. More specifically, the umbrella effect makes an X-ray scattering profile broaden toward the low-angle side if the scattering angle $2\theta$ is 90° or less, and toward the high-angle side if the scattering angle $2\theta$ is 90° or more.

To analyze the diameters of the particles contained in the sample, a scattering profile is utilized in a low-angle region thereof, for example, about 0° to 8° for CuKα rays. Thus, an umbrella effect is observed, i.e., the phenomenon that an X-ray scattering profile broadens toward the low-angle side. The correction of slits, which relates to the invention, is carried out to compensate for this umbrella effect.

(B) If incident X-rays are emitted from a point focus of a X-ray source and a converging mirror or a pinhole slit are provided in the incident-side region, the sample is irradiated with X-rays having a small scattering angle. An umbrella effect observed when X-rays having a small scattering angle are incident on the sample will be explained below. The smaller the scattering angle 2θ, the larger the curvature each Debye ring $\underline{D}$ has. That is, the closer each ring is to the right in FIG. 5, the larger its curvature. The larger its curvature is, the more prominent the umbrella effect. The correction of the slit is important, particularly in the case where particles or holes that scatter the X-rays are large. This is because the scattering profile is characterized by small scattering angles 2θ when the particles or holes are large.

To compensate for the umbrella effect defined above, two scattering vectors are calculated. The first scattering vector extends in the 2θ-rotation direction that lies in the scattering plane. The second vector extends in the vertical direction, i.e., a direction that is perpendicular to the 2θ-rotation direction. The scattering vector $\underline{q}$ observed in this case is expressed as follows:

$$q = \sqrt{(q_H^2 + q_N^2)} \quad (1)$$

where $q_H$ is the scattering vector in the scattering plane and $q_N$ is the vertical vector that extends perpendicular to the vector $q_H$.

The scattering vector $\underline{q}$ can be given by the following general equation:

$$q = (4\pi/\lambda)\sin(2\theta/2) \quad (2)$$

where 2θ is the scattering angle and λ is the wavelength of the X-rays.

(C) The scattering intensity $I_{obs}(q_N)$ obtained by performing slit correction for the true scattering intensity $I_{true}(\sqrt{(q_H^2 + q_N^2)})$ is:

$$I_{obs}(q_N) = \int_{-\infty}^{\infty} W(q_N) \cdot I_{true}(\sqrt{(q_H^2 + q_N^2)}) dq_N \quad (3)$$

where $W(q_N)$ is the intensity distribution in the vertical direction and $\int_{-\infty}^{\infty}$ is an integration for $-\infty$ to $+\infty$.

The equation (3) gives the intensity distribution in the vertical scattering direction, i.e., slit function $W(q_N)$. In addition, the true scattering intensity $I_{true}(\sqrt{(q_H^2 + q_N^2)})$ is obtained if the scattering intensity $I_{obs}(q_N)$ is actually measured. If the slit function $W(q_N)$ is given as a relatively simple function, the true scattering intensity $I_{true}(\sqrt{0(q_H^2 + q_N^2)})$ can be obtained by performing the calculation expressed by the equation (3).

If the slit function $W(q_N)$ may be complex, rendering it difficult to calculate the true scattering intensity $I_{true}(\sqrt{(q_H^2 + q_N^2)})$. In this case, a suitable model function $I_{model}$ is set for the true scattering intensity $I_{true}(\sqrt{(q_H^2 + q_N^2)})$ and is substituted in the equation (3). A scattering intensity $I_{calc}$ is thereby obtained. It is then determined whether the scattering intensity $I_{calc}$ thus obtained coincides with the scattering intensity $I_{obs}(q_N)$ actually measured. If the intensity $I_{calc}$ coincides with the intensity $I_{obs}(q_N)$, the model function $I_{model}$ is found to be the true scattering intensity $I_{true}(\sqrt{(q_H^2 + q_N^2)})$.

If the scattering intensity $I_{calc}$ does not coincide with the intensity $I_{obs}(q_N)$ actually measured, the fitting parameter of the model function $I_{model}$ is changed to another value. The calculation of the equation (3) and the comparing of the calculated scattering intensity and measured intensity are repeated, each time changing the model function $I_{model}$, until the calculated scattering intensity coincides with the measured intensity.

(D) The vertical angle at the incident side and the vertical angle at the receiving side will be explained, and then it will be described how to compensate for the umbrella effect and how to find the slit function $W(q_N)$. The slit function $W(q_N)$ is determined by the properties of the optical system employed, such as the heights of the slits and the inter-slit distances. Consider the optical system illustrated in FIG. 6.

As FIG. 6 depicts, the incident optical system comprises a multi-layered mirror 11 and a slit-collimation unit 12. The incident optical system, therefore, has high resolution in the direction of 2θ-rotation direction, that is, a direction in the scattering plane, or a direction parallel to the plane of FIG. 6. In the incident optical system, the vertical angle, i.e., an angle at which the rays diverge in the direction perpendicular to the plane of FIG. 6, is large unless a converging mirror accompanied by a point focus or pinhole slits are used.

FIG. 7 shows the vertical angle on the incident side and the X-ray irradiation height that depends on this angle. The X-ray irradiation height, which is determined by the optical system, may be larger than the height of the sample. If this is the case, the scattering of ray in the $q_N$ direction depends on the height of the sample. On the other hand, if the X-ray irradiation height may be smaller than the height of the sample, the scattering of ray in the $q_N$ direction will depend on the X-ray irradiation height that is determined by the optical system.

FIG. 8 illustrates the vertical angle on the receiving side, which is determined by the receiving side optical system, and also the X-ray emergence height that depends on this angle. The receiving side optical system performs double-slit collimation. Therefore, the resolution is high in the 2θ-rotation direction, i.e., a direction in the scattering plane, but low in the vertical direction. FIG. 8 depicts the vertical angle that is determined by the optical system and the X-ray irradiation height at the sample. If the height of the sample is smaller than the X-ray irradiation height at the sample, the vertical angle is determined by the height of the sample.

(E) The relation between the intensity of the rays applied to the sample and the intensity of the scattered rays will be explained. Note that the intensity of the rays applied depends upon the position where the X-rays are applied to the sample. That is, the relation between the intensity of the rays applied, which depends on the angle formed by lines of sight extending from the focus, and the intensity of the scattered rays, which depends on this angle, will be described.

If a light source or a propagation-ray source having a line focus is used as shown in FIGS. 7 and 8, the vertical angle is large. As a result, the X-ray irradiation height at the sample, i.e., the center of a goniometer, is larger than the height of the focus and the height of the slit, which are components of the optical system. The intensity of X-rays incident on the sample changes in the direction of height of the sample in accordance with the angle formed by lines of sight that extends to the focus from a position in the direction of height of the sample. Also, the intensity of X-rays radiant from the sample changes in the vertical direction in accordance with the angle formed by lines of sight that extends to the detector from a position in the direction of height of the sample.

In FIG. 9, the focus is completely seen from the midpoint, i.e., the point of Y=0, of the sample. The X-rays applied are therefore most intense at the midpoint at which Y=0. Also, since the angle formed by lines of sight is large on the receiving side, too, the intensity measured is proportionally high. On the other hand, the angles formed by lines of sight, extending from positions Y=Y1 and Y=Y2, both remote from the midpoint Y=0, are small. Hence, the X-rays applied have low intensity at these positions Y1 and Y2. The intensity of the X-rays, which is measured on the receiving side, is low. This is because the height of the slit restricts the scattered rays on the receiving side. As such, the intensity of the X-rays applied and the intensity of the X-rays scattered depend upon the position Y where the sample is irradiated with the X-rays.

(F) The scattering angle, at which X-rays are scattered in the vertical direction, depends on the position where the sample is irradiated with the X-rays. The scattering angle will be described. As mentioned above, the angle formed by lines of sight that extend to the focus and the detector, respectively, may differ from each other, depending on the position Y where the sample is irradiated with the X-rays. If these angles are different, vertical components of the scattering angle will be generated. The vertical components of the scattering angle will be explained.

FIG. 10 shows the intensity distribution of the X-rays incident on the sample, which is observed when the sample is irradiated with the X-rays at the mid-position Y=0. In FIG. 10, $\theta_{N\text{-}in}^{max}$ depicts the maximum angle formed by line of sight of the focus, and $\theta_{N\text{-}in}^{min}$ depicts the minimum angle formed by line of sight of the focus. $\theta_{N\text{-}in}^{max}$ and $\theta_{N\text{-}in}^{min}$ are angles that are measured along a direction shown by $\theta_{N\text{-}in}$. FIGS. 11 to 13 represent, respectively, the intensity distributions of X-rays radiant from the sample with respect to the scattering angle $2\theta_N$ when the X-rays are incident on the sample at the mid-position Y=0, by an angle of $\theta_{N\text{-}in=0}$, $\theta^{N\text{-}in\,max}$ and $\theta_{N\text{-}in}^{min}$, respectively. If the X-rays are applied to the sample, at the mid-position Y=0, by an angle range from $\theta_{N\text{-}in}^{min}$ to $\theta_{N\text{-}in}^{max}$, the total X-ray intensity distribution observed at the mid-position Y=0 in the vertical direction is given as the sum of the intensity distributions calculated for the above-mentioned angle range.

FIG. 14A shows the vertical angle $\theta_{N\text{-}in}$ on the incident side and the vertical angle $\theta_{N\text{-}OUT}$ on the receiving side. In this case, the total scattering intensity at the X-ray irradiation position Y=0 is obtained, as shown in FIG. 14D, by the convolution of the intensity distribution on the vertical angle $\theta_{N\text{-}in}$ as shown in FIG. 14B and the intensity distribution on the vertical angle $\theta_{N\text{-}OUT}$ as shown in FIG. 14C. The intensity distribution on the vertical angle $\theta_{N\text{-}in}$ means the X-ray intensity distribution on the incident side. And the intensity distribution on the vertical angle $\theta_{N\text{-}OUT}$ means the X-ray intensity distribution on the receiving side. FIG. 14D represents the slit function $W(q_N; Y=0)$ that is applied for the X-ray irradiation position Y=0.

Note that convolution is a data-processing method generally known in the field of data processing. Assume that two functions $m(\theta)$ and $n(\theta)$ are available, and the value of $\theta$ in that one of these functions is changed from $-\infty$ to $+\infty$. Then, the mutually overlapping parts of $m(\theta)$ and $n(\theta)$ change. The convolution is a function that represents this change. Hence, the convolution of $m(\theta)$ and $n(\theta)$ is expressed as:

$$F(\theta) = \int -\infty^\infty m(\theta') \times n(\theta' - \theta) d\theta' \tag{4}$$

where $\int -\infty^\infty$ is an integration for the range of $-\infty$ to $+\infty$. In the above-mentioned slit correction, $m(\theta)$ corresponds to $\theta_{in}(\theta)$, and $n(\theta)$ corresponds to $\theta_{out}(\theta)$.

(G) The convolution will be briefly described. Assume that the intensity distribution on the incident side and the intensity distribution on the receiving side are $\theta_{in}(\theta)$ and $\theta_{out}(\theta)$ shown respectively in FIG. 15. Then, the convolution is determined by changing either $\theta_{in}(\theta)$ or $\theta_{out}(\theta)$ from $-\infty$ to $+\infty$, as will be described below in detail with reference to FIGS. 16–21.

In the case shown in FIG. 16, the overlapping area of $\theta_{in}(\theta)$ and $\theta_{out}(\theta)$ is "0" when $\theta_{in}$ is changed to $-8$. That is, the convolution is "0." Since no parts having intensity of "1" overlap in FIG. 16, the convolution is still "0." When $\theta_{in}$ is further changed toward $+\infty$, more precisely to $-6$, as is illustrated in FIG. 17, the overlapping area is "1."

Further, $\theta_{in}$ is changed toward $+\infty$, to $-5$, for example, as illustrated in FIG. 18. Then, the overlapping area is "2." Still further, $\theta_{in}$ is changed toward $+\infty$, to $-2$ as shown in FIG. 19, the overlapping area increases to "5." Assume that $\theta_{in}$ is further changed toward $+\infty$, to 0 as shown in FIG. 20, the overlapping area is "5."

The convolution is obtained by changing $\theta_{in}$ toward $+\infty$ and adding the overlapping areas, each determined for each value of $\theta_{in}$. FIG. 21 illustrates the convolution thus obtained.

(H) The slit function $W(qN)$ given by the equation (3) can be obtained by adding the slit functions $W(qN; Y)$ at all X-ray irradiation positions Y. For example, the slit function at the position of Y=Y1 shown in FIG. 9 is derived as shown in FIG. 22D, and the slit function at the position of Y=Y2 shown in FIG. 9 is derived as illustrated in FIG. 23D.

(I) Three slit functions have been calculated for three points, i.e., Y=0, Y=Y1 and Y=Y2. If the sample is irradiated at these three points only, the slit function $W(q_N)$ is given as the sum of the three slit functions, $W(q_N; Y=Y0)$, $W(q_N; Y=Y1)$ and $W(q_N; Y=Y2)$ for the three points Y0, Y1 and Y2. FIG. 24 depicts the slit function thus calculated for the case where the sample is irradiated at these three points Y0, Y1 and Y2.

The slit function shown in FIG. 24 cannot be applied in practice, because it is calculated for only a few points where the sample is irradiated with the X-rays. To provide a slit function that can be used in practice, the sample is irradiated with X-rays at many points. FIG. 25 shows a slit function that has been calculated by irradiating the sample with X-rays at 100 points. The following conditions were set to obtain this practical slit function.

The heights of the components shown in FIG. 9:

| Height H1 of the filament | H1 = 10 mm |
|---|---|
| Height S1 of the slit S1 | S1 = 10 mm |
| Height S2 of the slit S2 | S2 = 10 mm |
| Height of S of the sample S | S = 100 mm |
| Height S3 of the slit S3 | S3 = 20 mm |
| Height S4 of the slit S4 | S4 = 20 mm |

Height H2 of the X-ray window of counter H2=20 mm

Distances in FIG. 9:

| Distance between focus and slit S1 | 161 mm |
|---|---|
| Distance between slits S1 and S2 | 200 mm |
| Distance between slit S2 and sample S | 264 mm |
| Distance between sample S and slit S3 | 340 mm |

-continued

| | |
|---|---|
| Distance between slits S3 and S4 | 70 mm |
| Distance between slit S4 and counter window | 10 mm |

The slit function shown in FIG. 25, if obtained, may be substituted in the equation (3) set forth above. Then, a scattering intensity can be determined, which is not influenced by the umbrella effect and which is therefore extremely accurate.

A sample-analyzing apparatus according to the present invention comprises: a propagation-ray source for emitting propagation rays that irradiate a sample; an incident beam slit provided between the propagation-ray source and the sample; detecting means for detecting propagation rays scattered again from the sample; a receiving side beam slit provided between the sample and the detecting means; slit-function outputting means for calculating and outputting a slit function from geometrical conditions input; model-function outputting means for outputting a model function containing fitting parameters for use in calculating an X-ray scattering intensity; function-calculating means for calculating an analysis function from the slit function and the model function; and parameter-optimizing means for determining a similarity between the analysis function calculated and a function actually measured, and for optimizing the fitting parameters contained in the model function, thereby to enhance the similarity between the analysis function calculated and the function actually measured.

The analyzing apparatus mentioned above has the slit-function output means that outputs a slit function. The slit function output by this means pertains to the slits used in the optical system actually employed. This helps to analyze the sample correctly.

Another analyzing apparatus according to this invention comprises: a propagation-ray source for emitting propagation rays that irradiate a sample; an incident beam slit provided between the propagation-ray source and the sample; detecting means for detecting propagation rays scattered again from the sample; a receiving side beam slit provided between the sample and the detecting means; slit-function outputting means for calculating and outputting a slit function from geometrical conditions pertaining to the incident beam slit and receiving side beam slit; model-function outputting means for outputting a model function containing fitting parameters for use in calculating an X-ray scattering intensity; function-calculating means for calculating an analysis function from the slit function and the model function; and parameter-optimizing means for determining a similarity between the analysis function calculated and a function actually measured, and for optimizing the fitting parameters contained in the model function, thereby to enhance the similarity between the analysis function calculated and the function actually measured.

The analyzing apparatus mentioned above also has slit-function output means that outputs a slit function. The slit function output by this means pertains to the slits used in the optical system actually employed. This helps to analyze the sample correctly.

In the analyzing apparatuses of the structure described above, the propagation rays may be X-rays or particle beams. Further, the particle beams may be neutron beams or electron beams.

In the analyzing apparatus of the structure specified above, it is desirable to determine the slit function from a variable that represents a position in a lengthwise direction of the sample, where the sample is irradiated with the propagation rays. Then, the slit function can be an accurate one more pertaining to the optical system than otherwise. The sample can therefore be analyzed with a higher precision.

In the analyzing apparatus of the structure specified above, it is desirable to determine the slit function on the basis of the fact that an angle formed by lines of sight which extends from the sample to the propagation-ray source through the incident beam slit and an angle formed by lines of sight which extends from the sample to the detecting means through the receiving side beam slit change in accordance with a position in a lengthwise direction of the sample. In this case, too, the slit function can be an accurate one more pertaining to the optical system than otherwise. The sample can therefore be analyzed with a higher precision.

In the analyzing apparatus of the structure specified above, it is desirable to determine the slit function from a convolution of two intensity distributions that the propagation rays assume at an incident side and receiving side of the sample, respectively. If so, the slit function can be an accurate one more pertaining to the optical system than otherwise. The sample can therefore be analyzed with a higher precision.

DETAILED DESCRIPTION OF THE PREFERRED EMBODIMENTS (First Embodiment)

An embodiment of the invention will be described, which are a sample-analyzing method and apparatus for use in the ordinary X-ray diffraction analysis that employs an X-ray diffraction apparatus.

Figure 1:
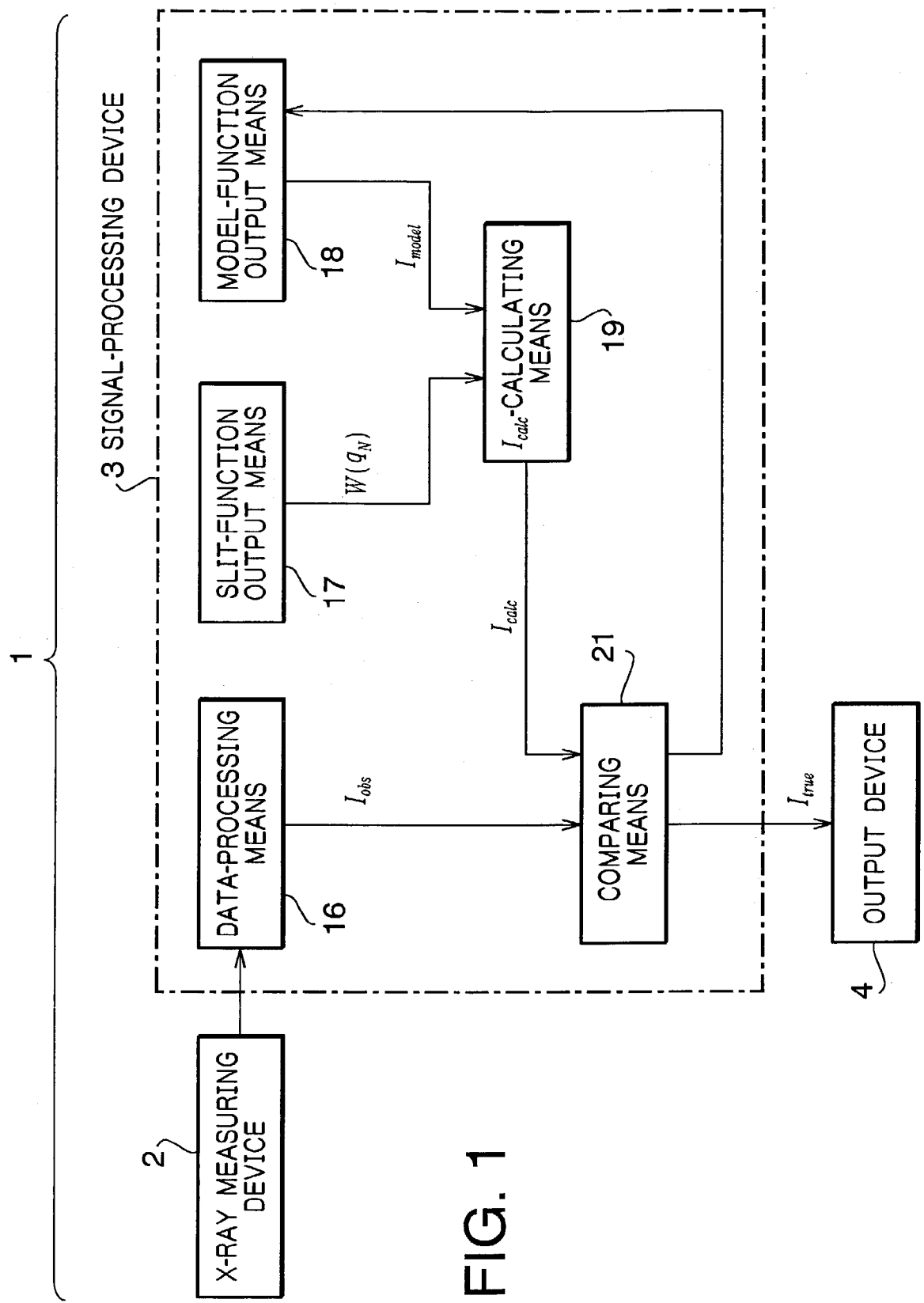
FIG. 1 is a block diagram of an embodiment of a sample-analyzing apparatus according to the present invention.

FIG. 1 shows a block diagram of a sample-analyzing apparatus 1 according to the present invention. The apparatus 1 has an X-ray measuring device 2, a signal-processing device 3, and an output device 4. The X-ray measuring device 2 applies X-rays, or propagation rays, to a sample, thereby to perform measuring on the sample. The signal-processing device 3 processes the signal output from the X-ray measuring device 2. The output device 4 displays the results of the process carried out by the signal-processing device 3, so that the results may be visually recognized.

Figure 6:
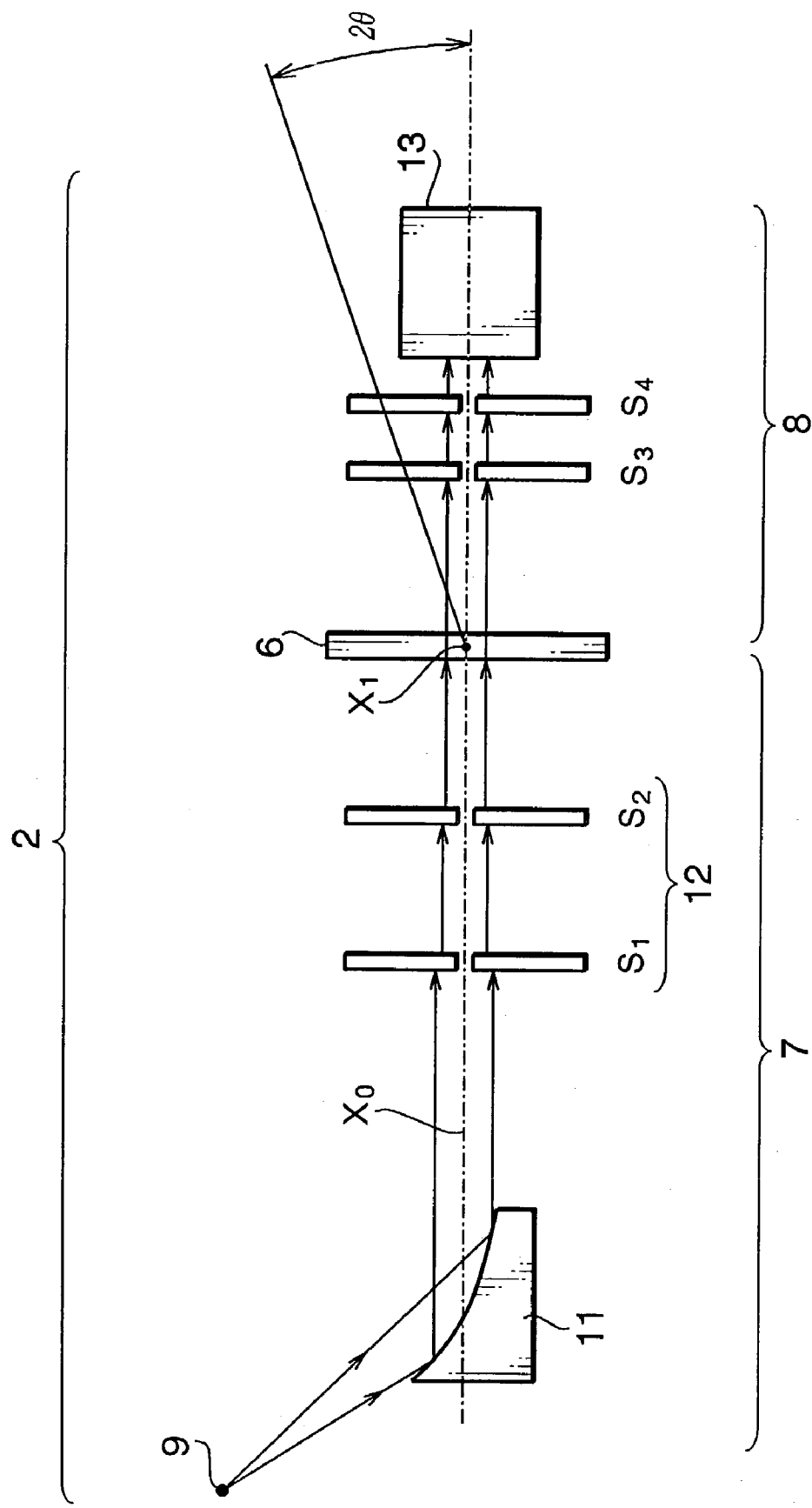
FIG. 6 is a plan view of the X-ray measuring device shown in FIG. 1.
Figure 7:
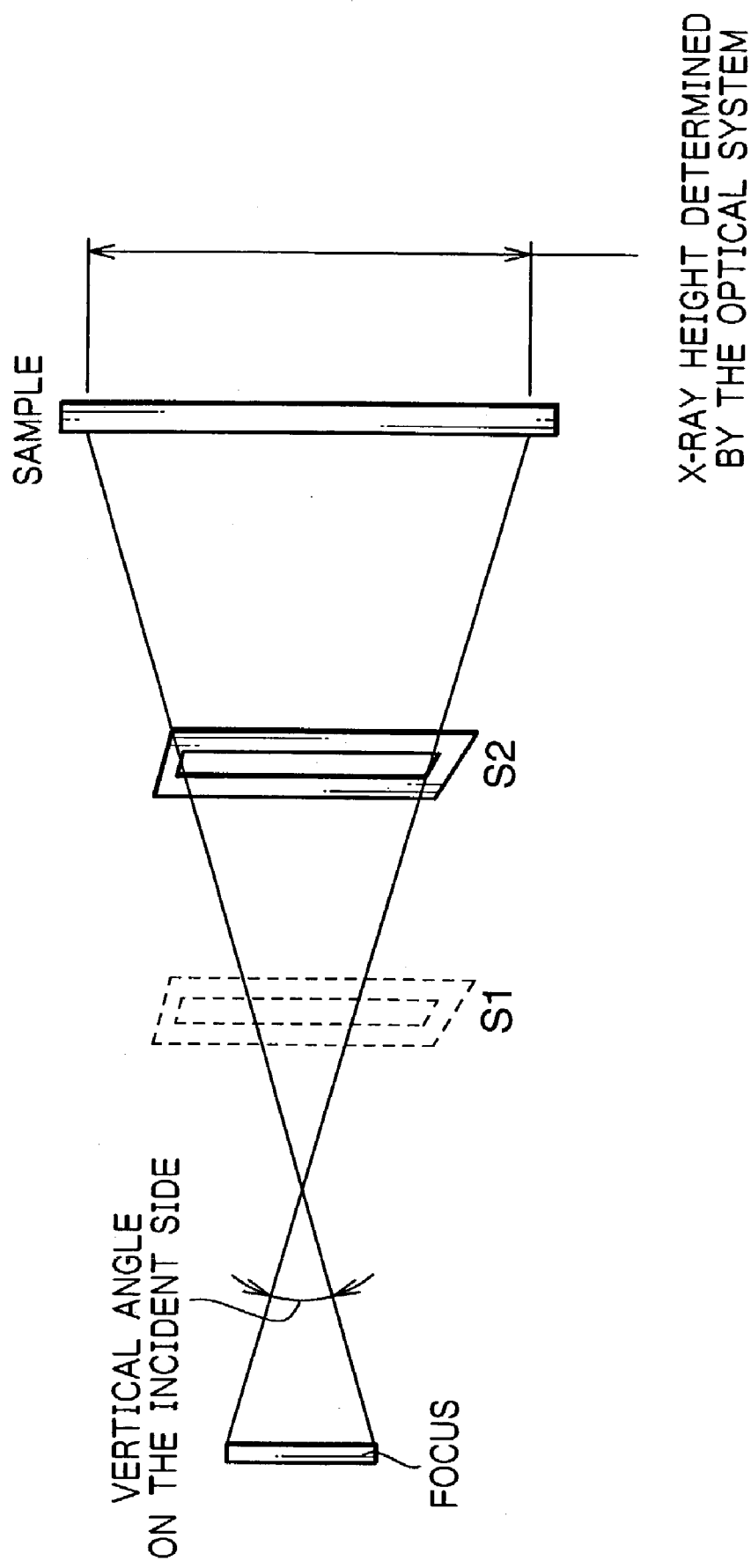
FIG. 7 is a diagram showing the input section, i.e., the incident side, of the X-ray optical system, for explaining how to find a slit function.
Figure 8:
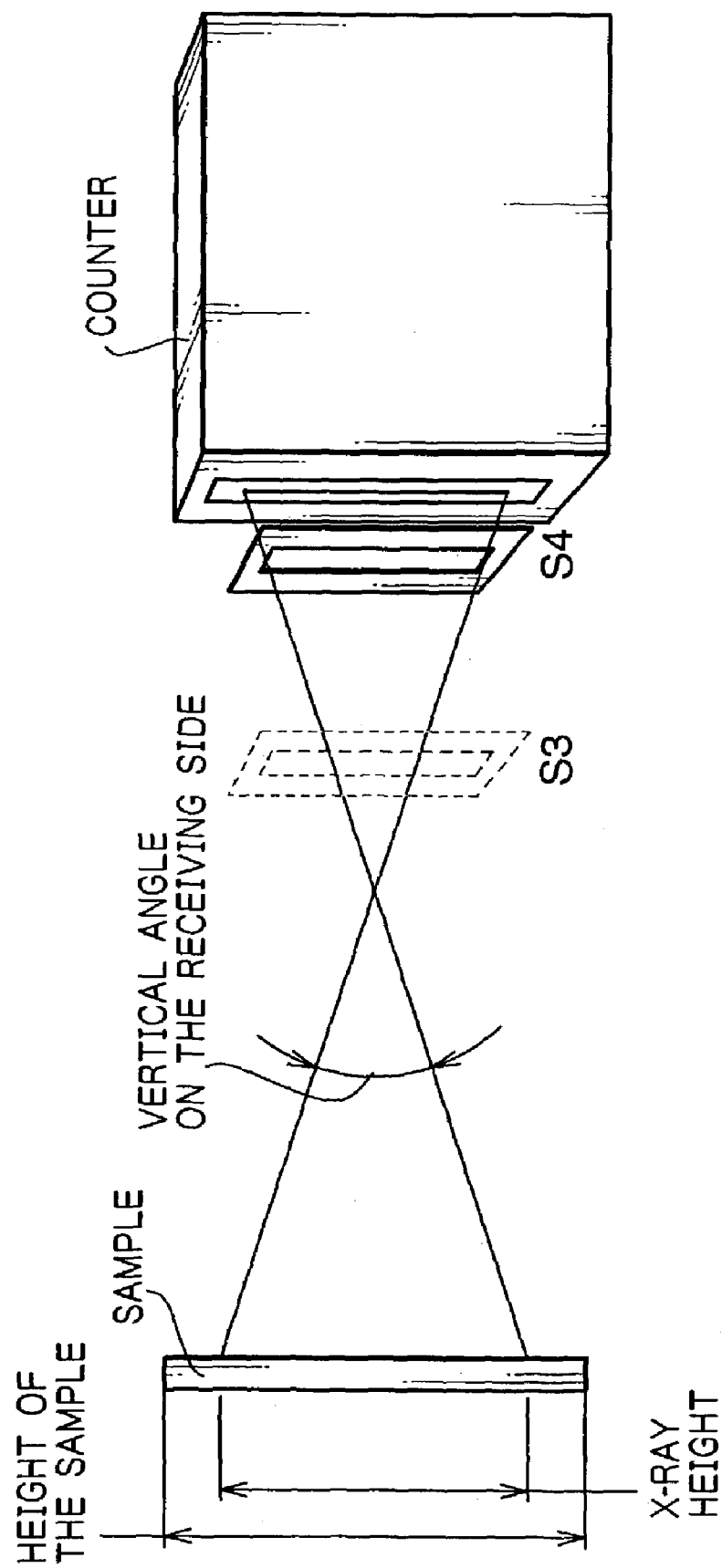
FIG. 8 is a diagram depicting the output section, i.e., the receiving side, of the X-ray optical system, for explaining how to find the slit function.
Figure 9:
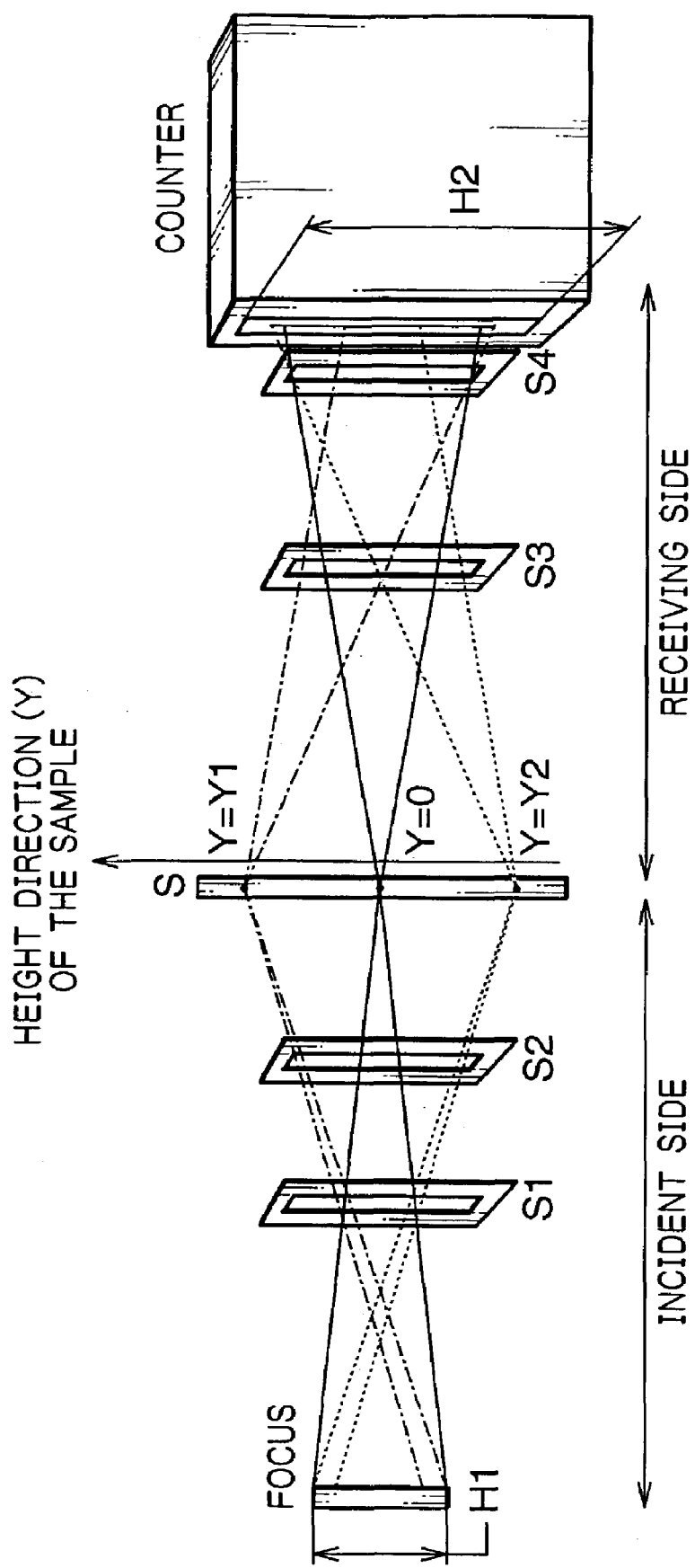
FIG. 9 is a diagram illustrating the entire X-ray optical system, for explaining how to find the slit function.
Figure 10:
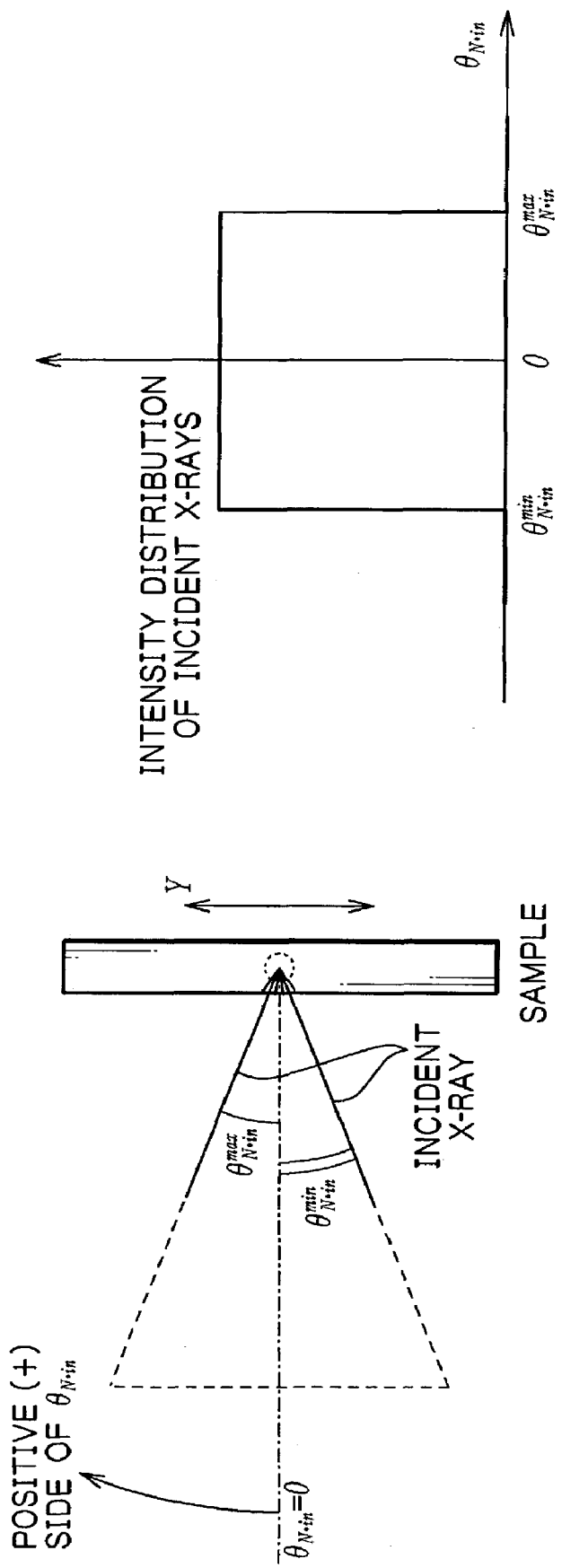
FIG. 10 is a diagram showing the angle of vertical divergence in the incident side of the optical system of FIG. 9, and illustrating the intensity distribution of incident X-ray component that diverges vertically.
Figure 11:
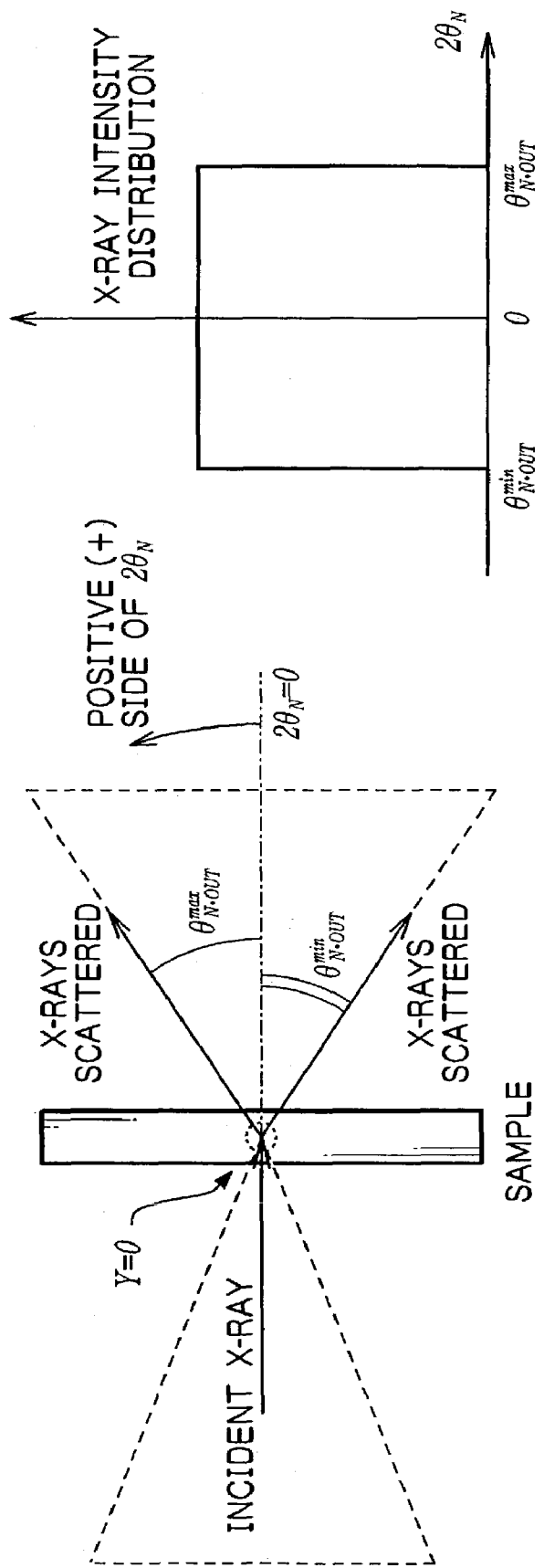
FIG. 11 is a diagram illustrating the scattering angle of the vertically diverging X-ray component and the intensity distribution of the X-ray, which are observed in the optical system of FIG. 9 when Y=0 and the incident angle of the X-rays=0°.
Figure 12:
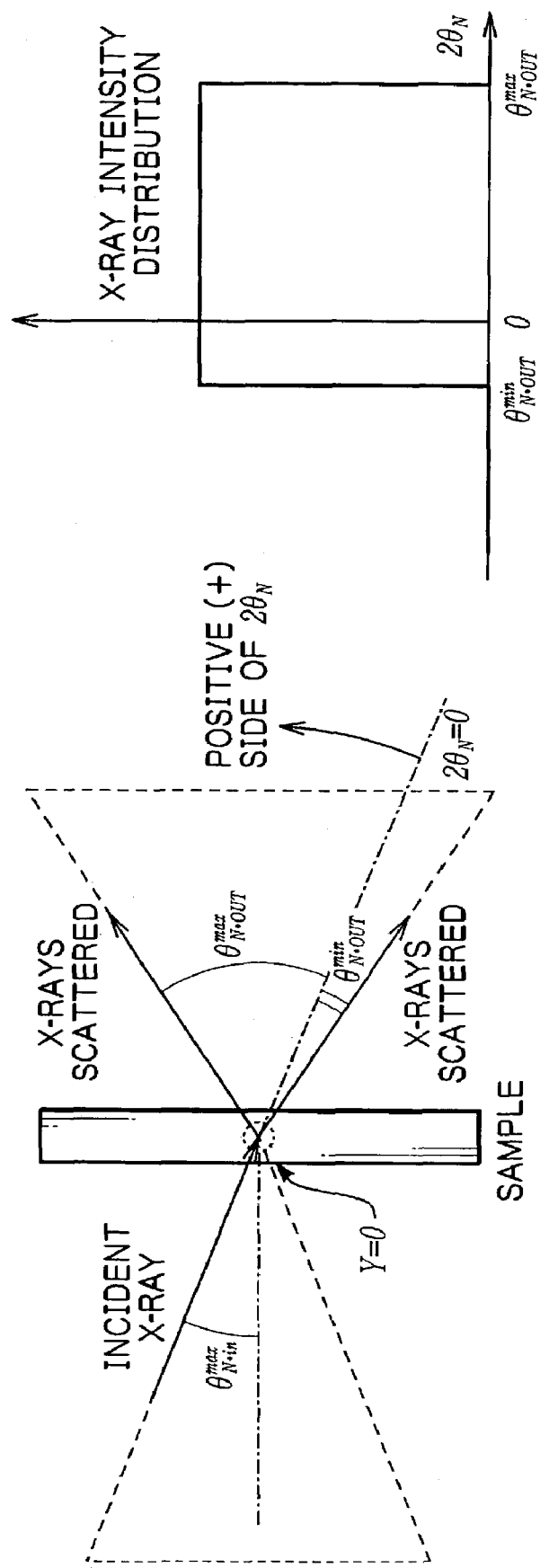
FIG. 12 is a diagram showing the scattering angle of the vertically diverging X-ray component and the intensity distribution of the X-ray, which are observed in the optical system of FIG. 9 when Y=0 and the incident angle of the X-rays=$\theta^{max}$.
Figure 13:
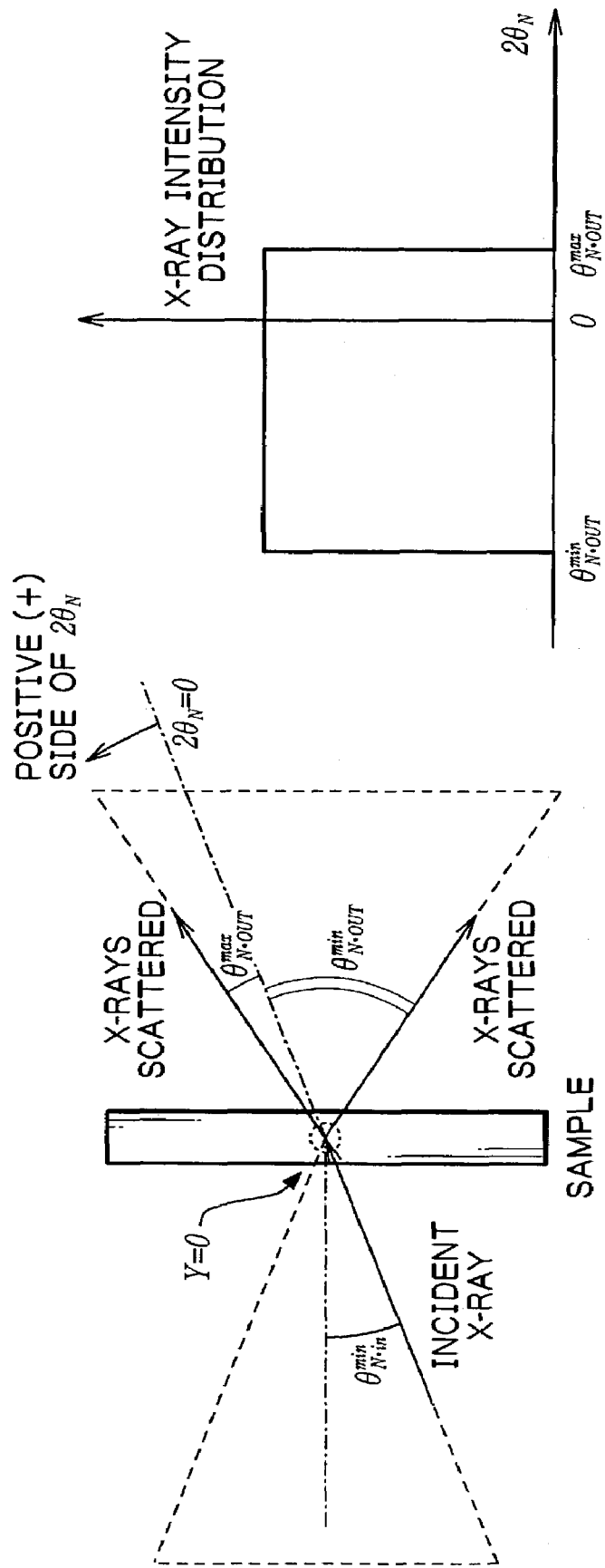
FIG. 13 is a diagram showing the scattering angle of the vertically diverging X-ray component and the intensity distribution of the X-ray, which are observed in the optical system of FIG. 9 when Y=0 and the incident angle of the X-rays=$\theta^{min}$.
Figure 14A:
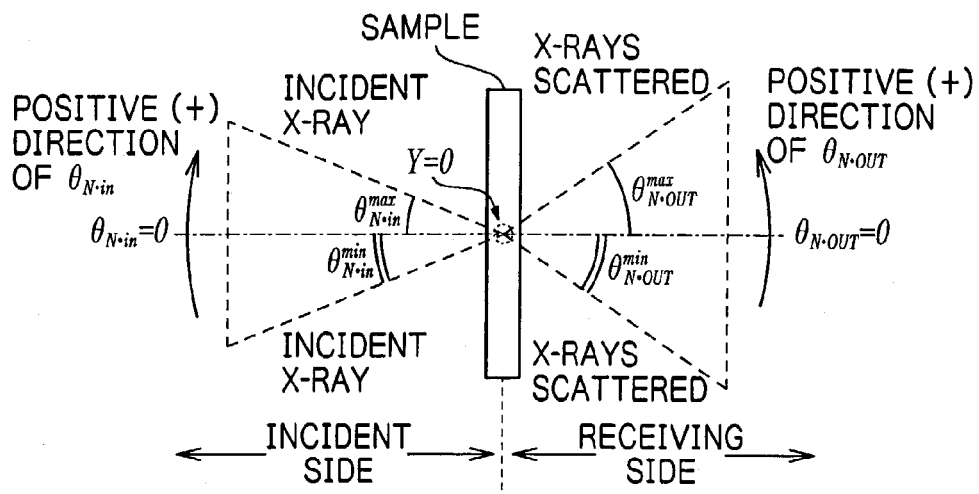
FIGS. 14A to 14D are diagrams that schematically explain how to find the slit function when Y=0.
Figure 14B:
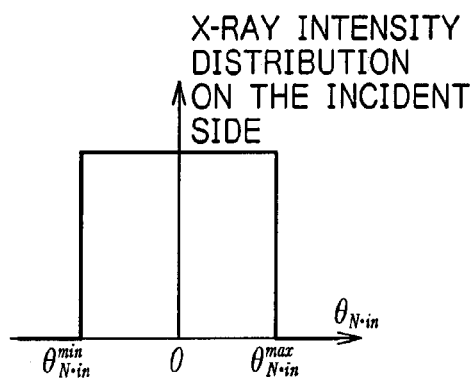
Figure 14C:
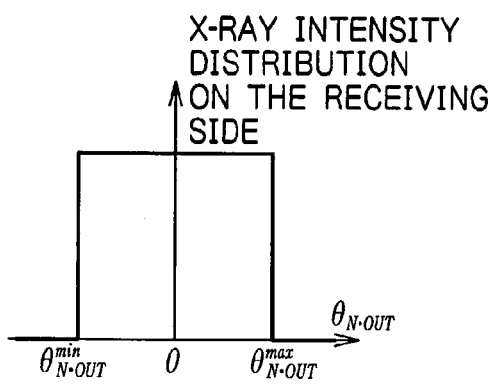
Figure 14D:
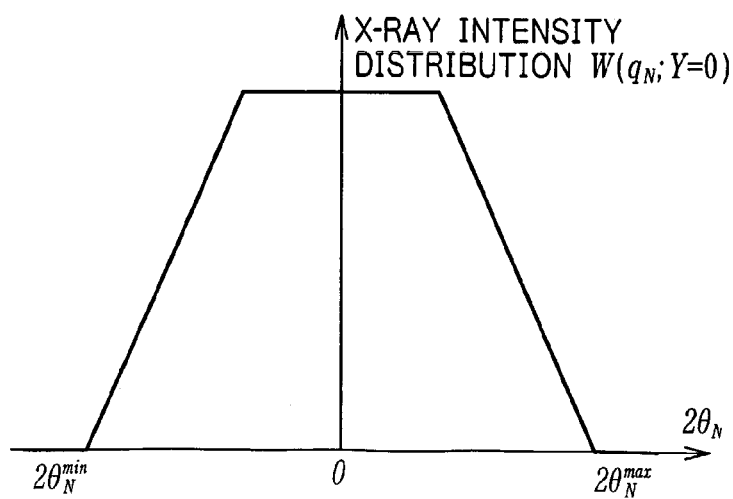
Figure 15:
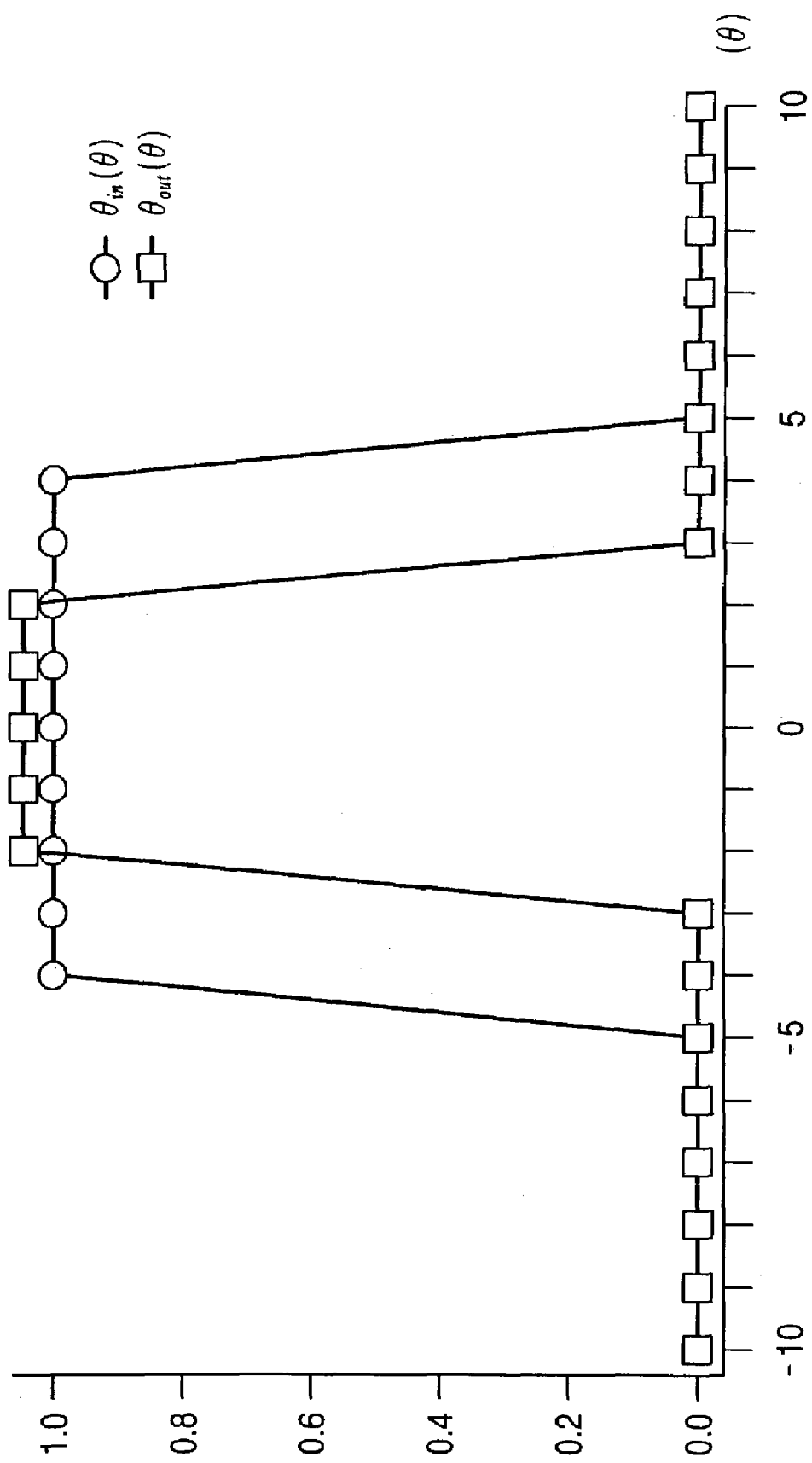
FIG. 15 is a graph for explaining convolution.
Figure 16:
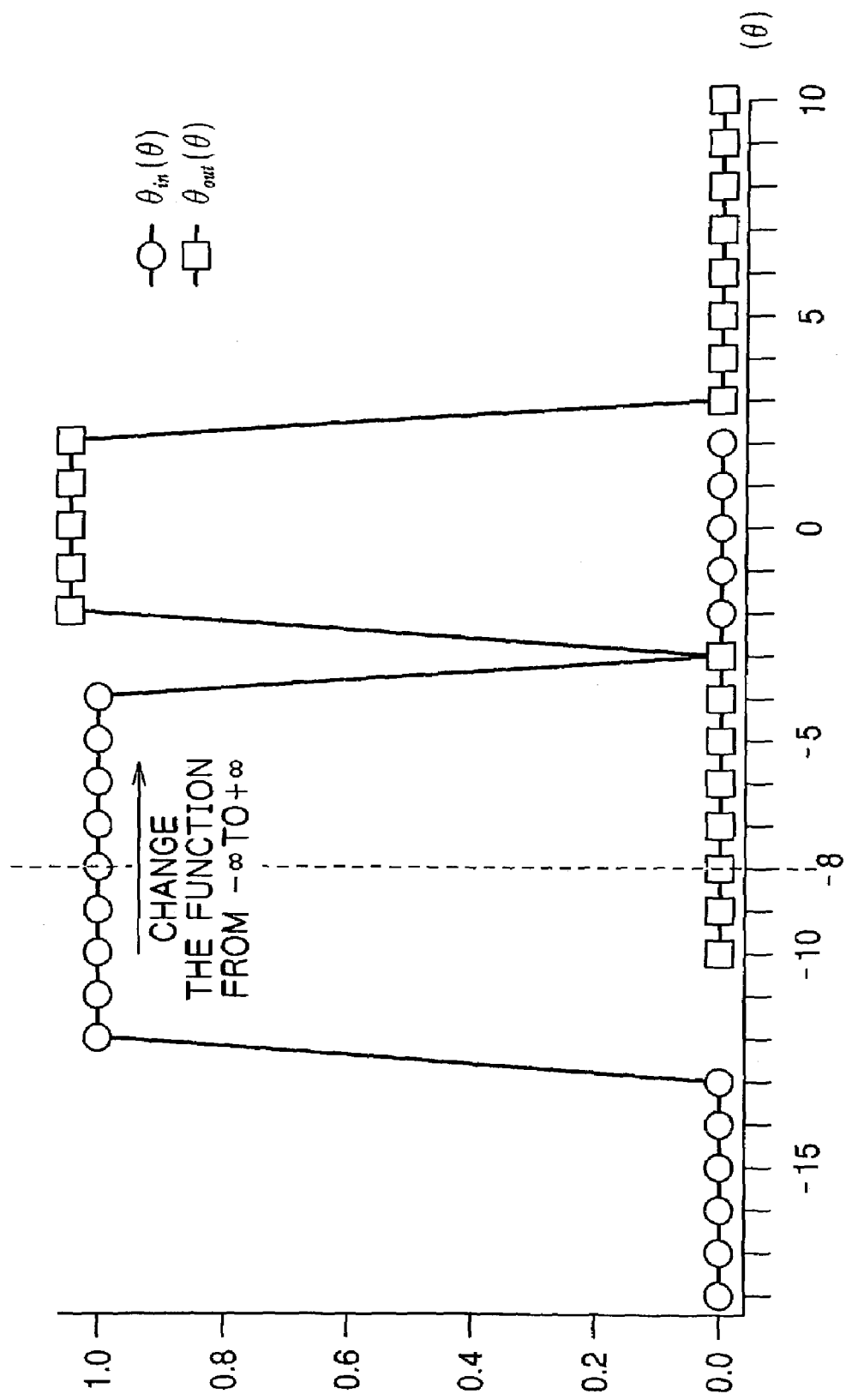
FIG. 16 is another graph for explaining the convolution.
Figure 17:
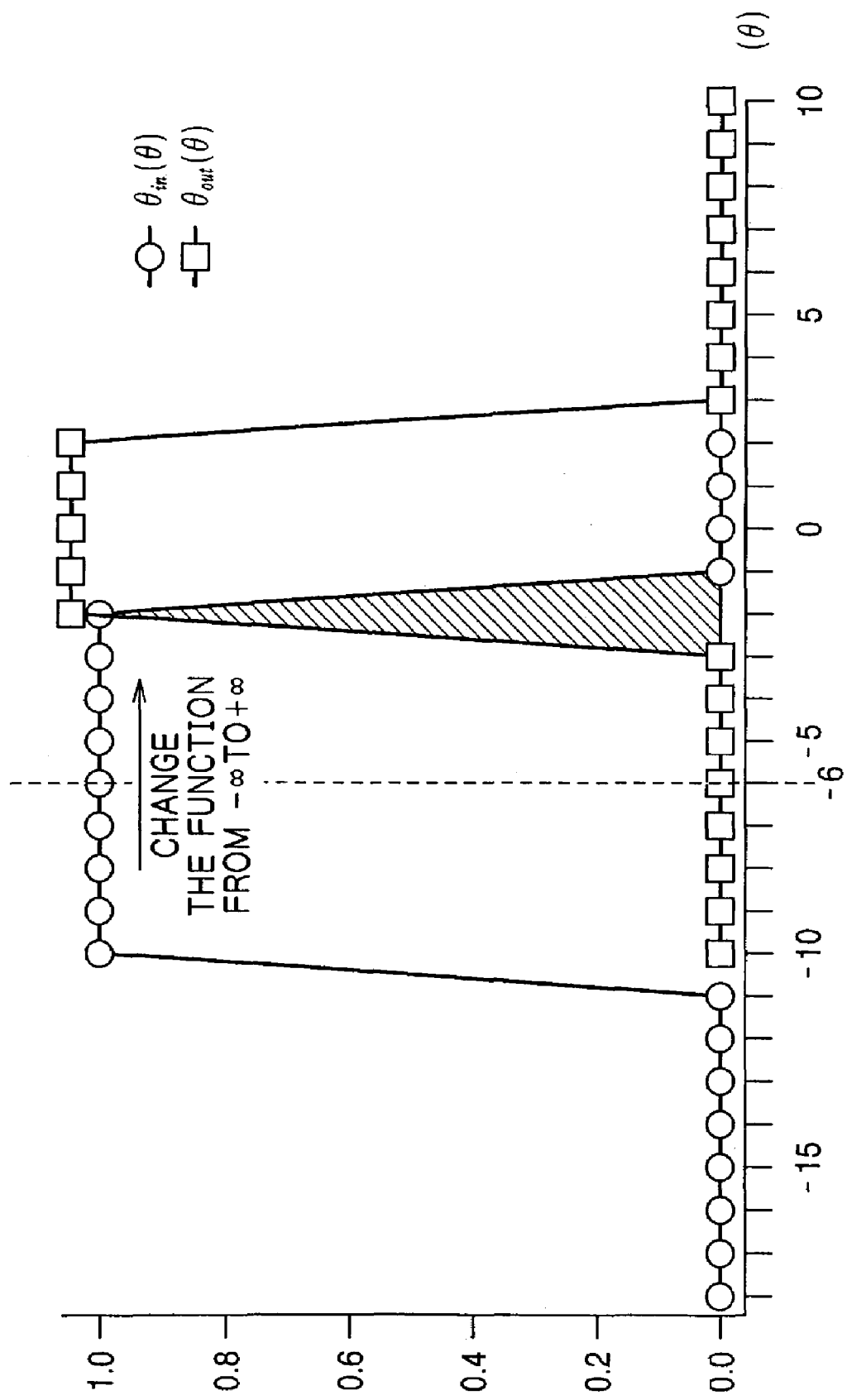
FIG. 17 is still another graph for explaining the convolution.
Figure 18:
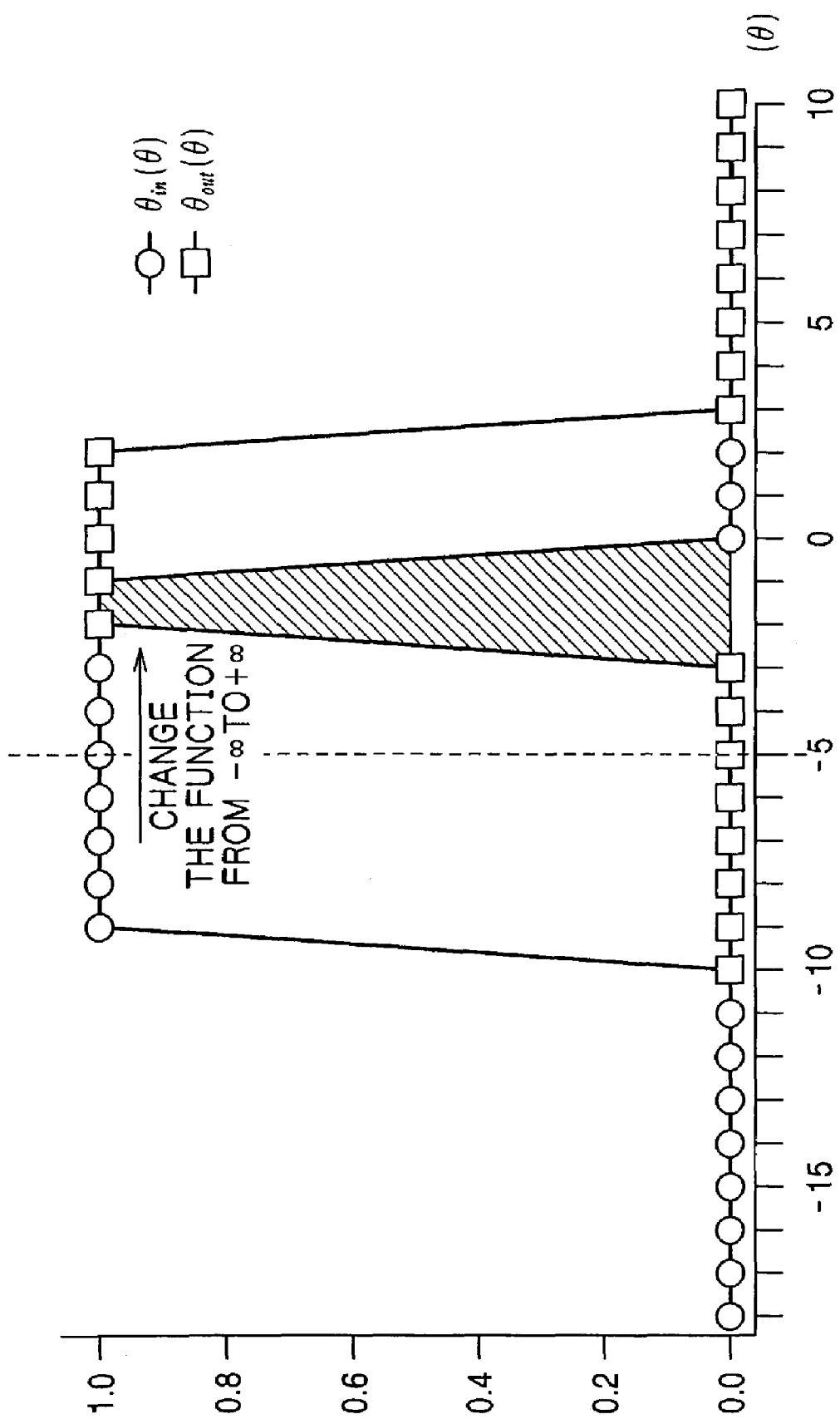
FIG. 18 is still another graph for explaining the convolution.
Figure 19:
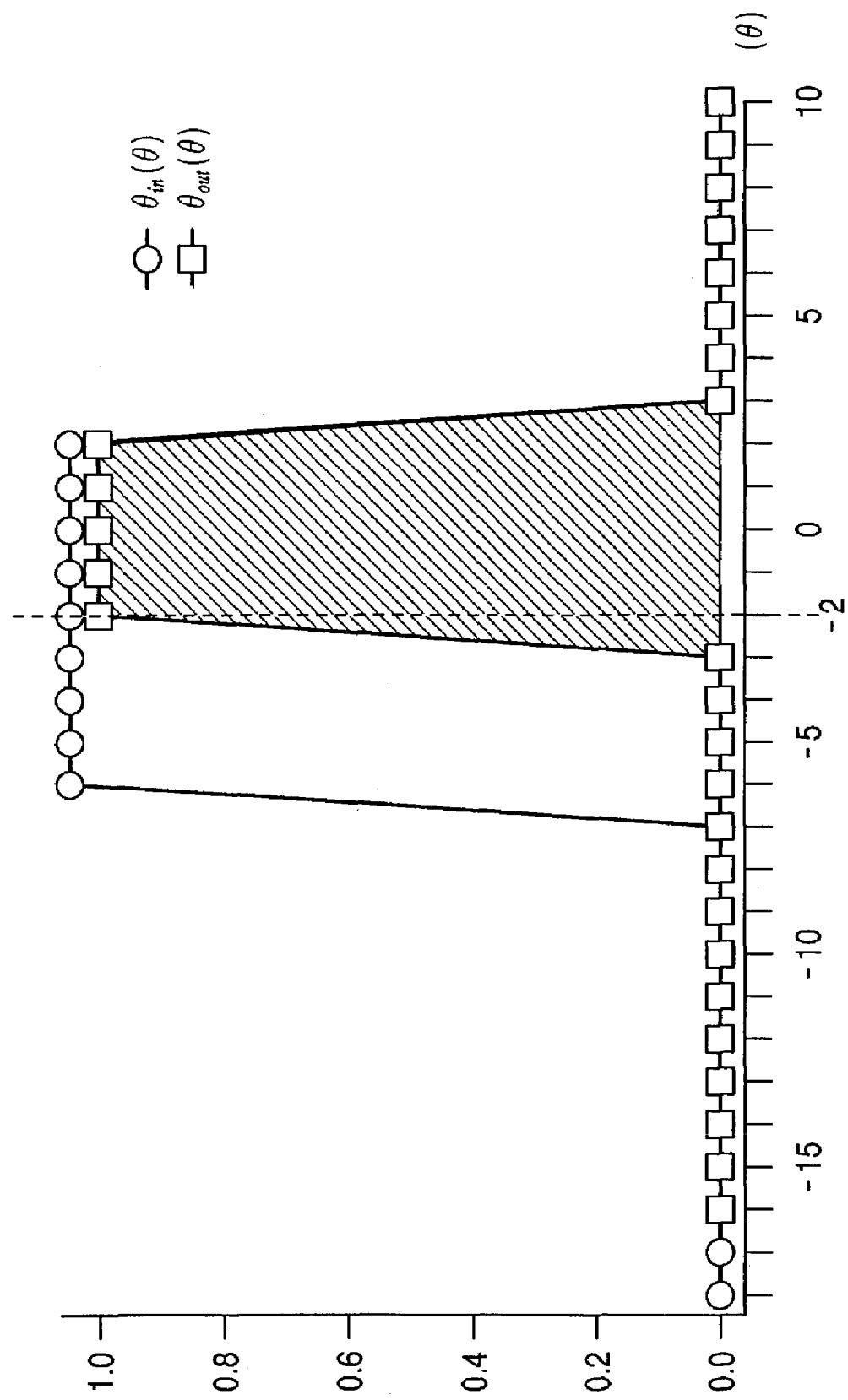
FIG. 19 is still another graph for explaining the convolution.
Figure 20:
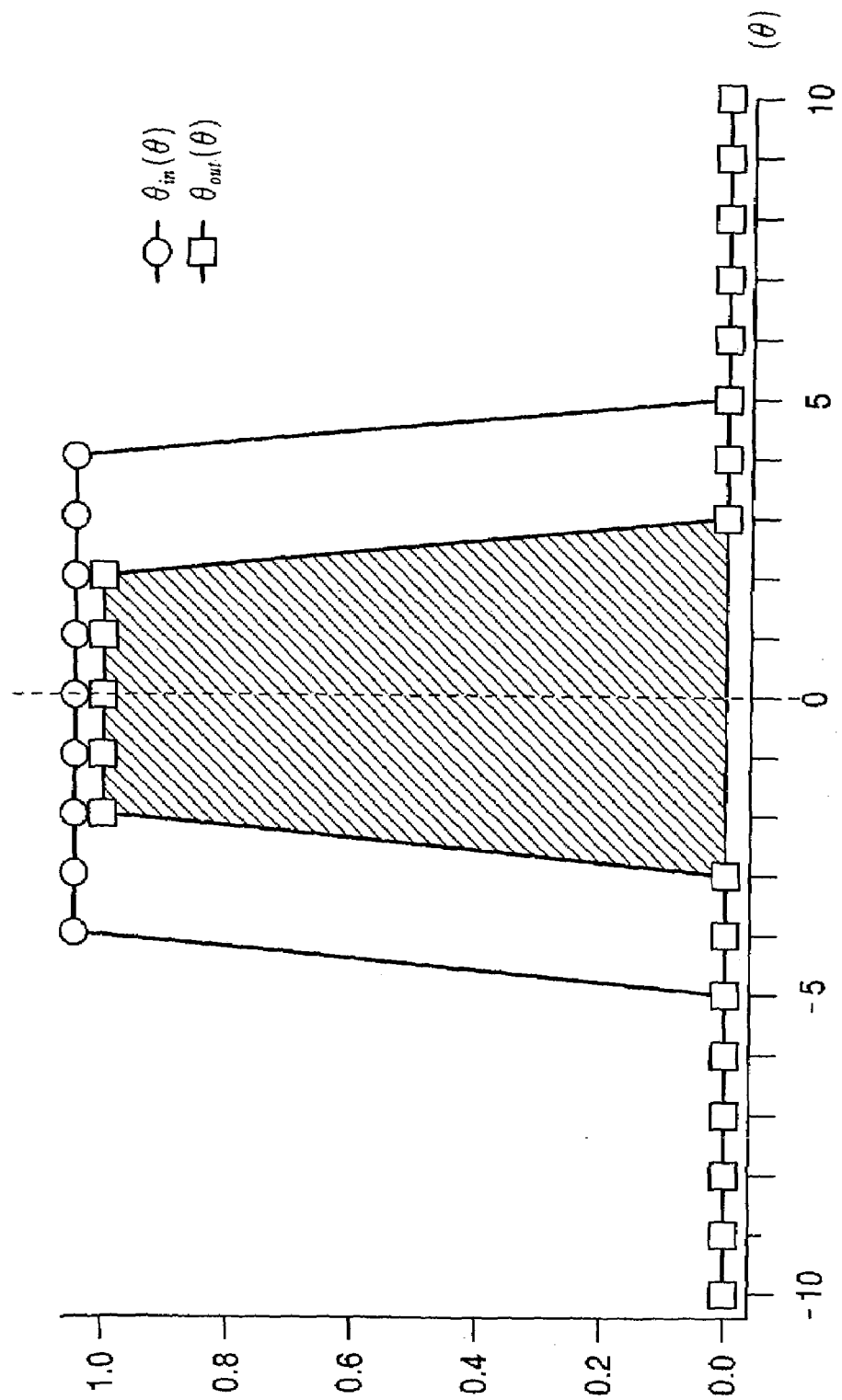
FIG. 20 is still another graph for explaining the convolution.
Figure 21:
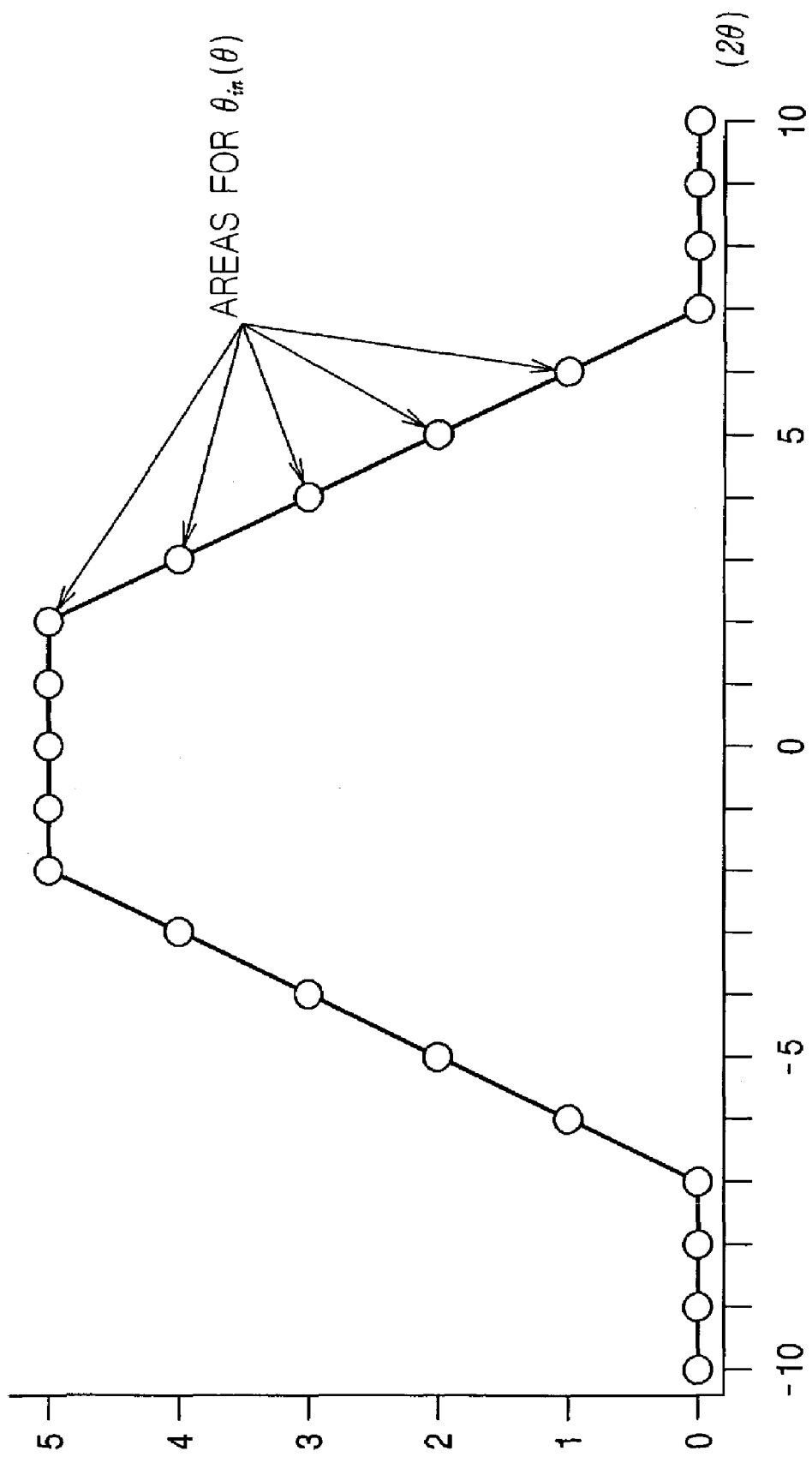
FIG. 21 is still another graph for explaining the convolution.
Figure 22A:
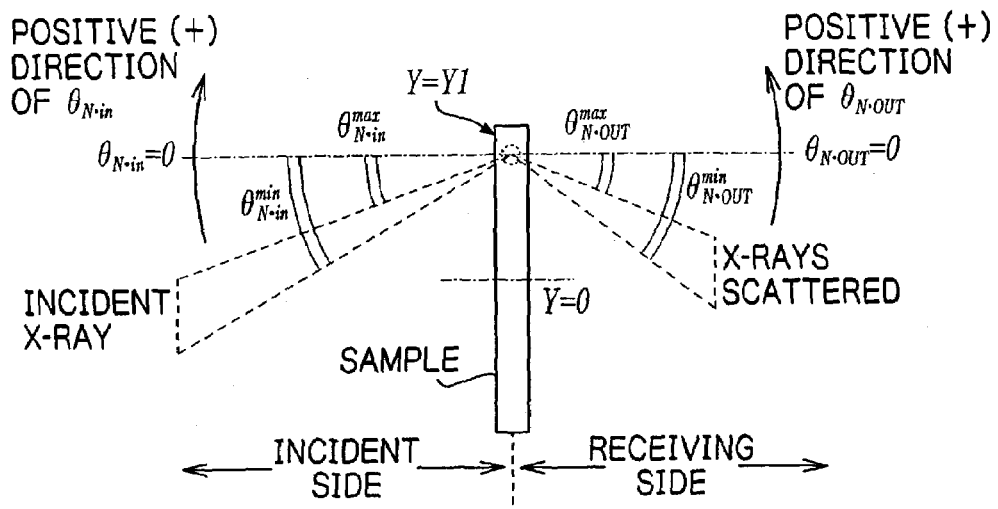
FIGS. 22A to 22D are diagrams that schematically explain how to find the slit function when Y=Y1.
Figure 22B:
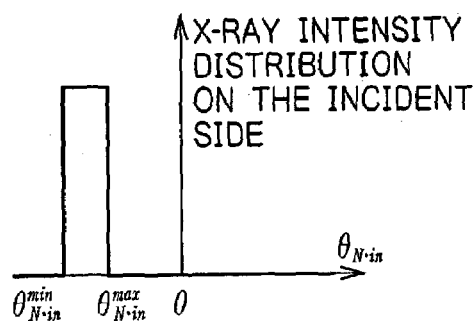
Figure 22C:
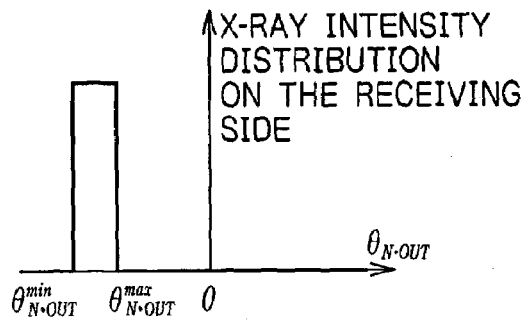
Figure 22D:
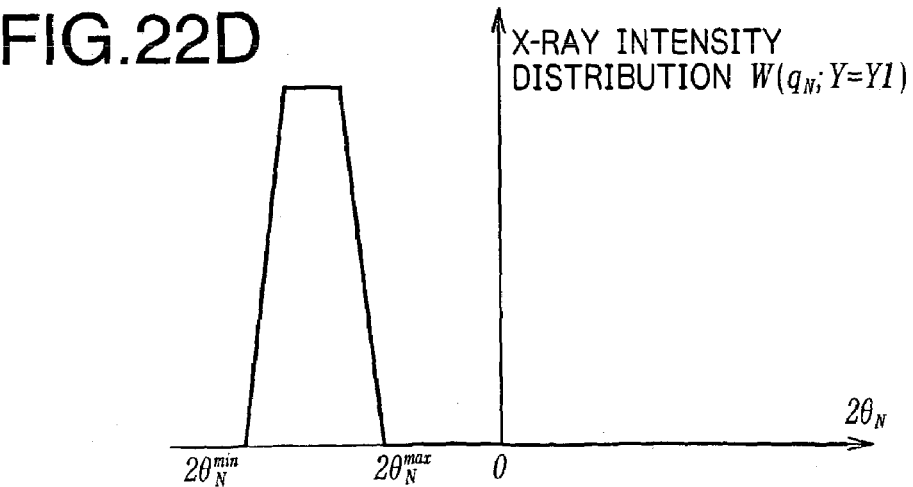
Figure 23A:
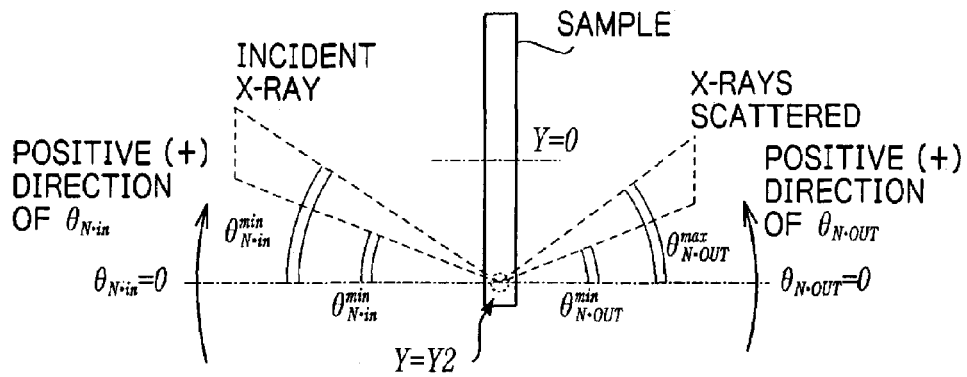
FIGS. 23A to 23D are diagrams that schematically explain how to find the slit function when Y=Y2.
Figure 23B:
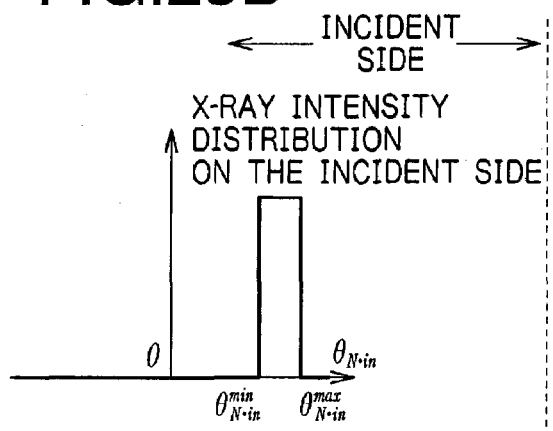
Figure 23C:
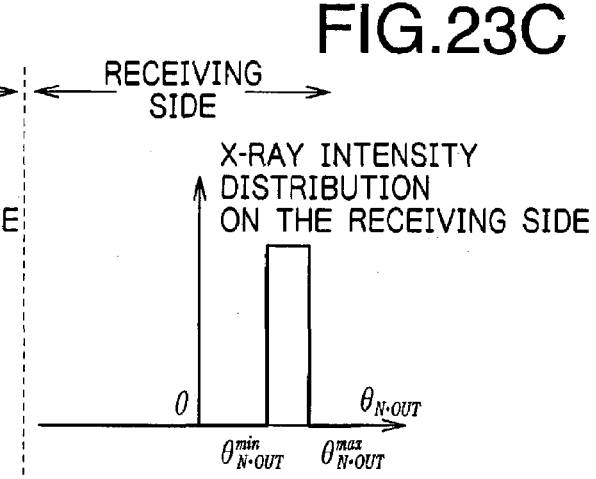
Figure 23D:
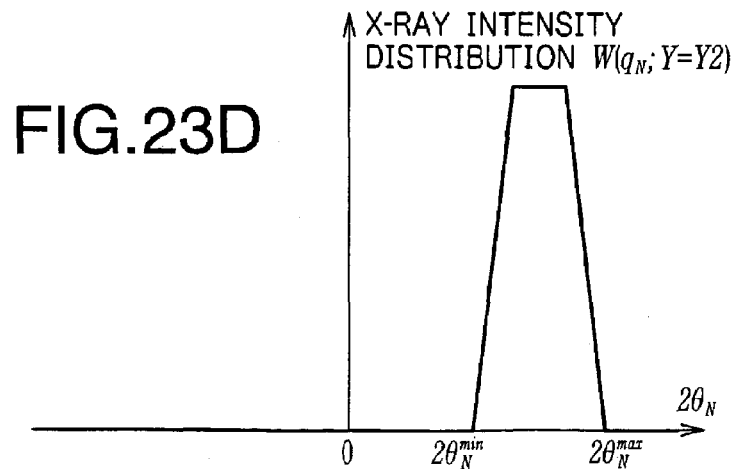
Figure 24:
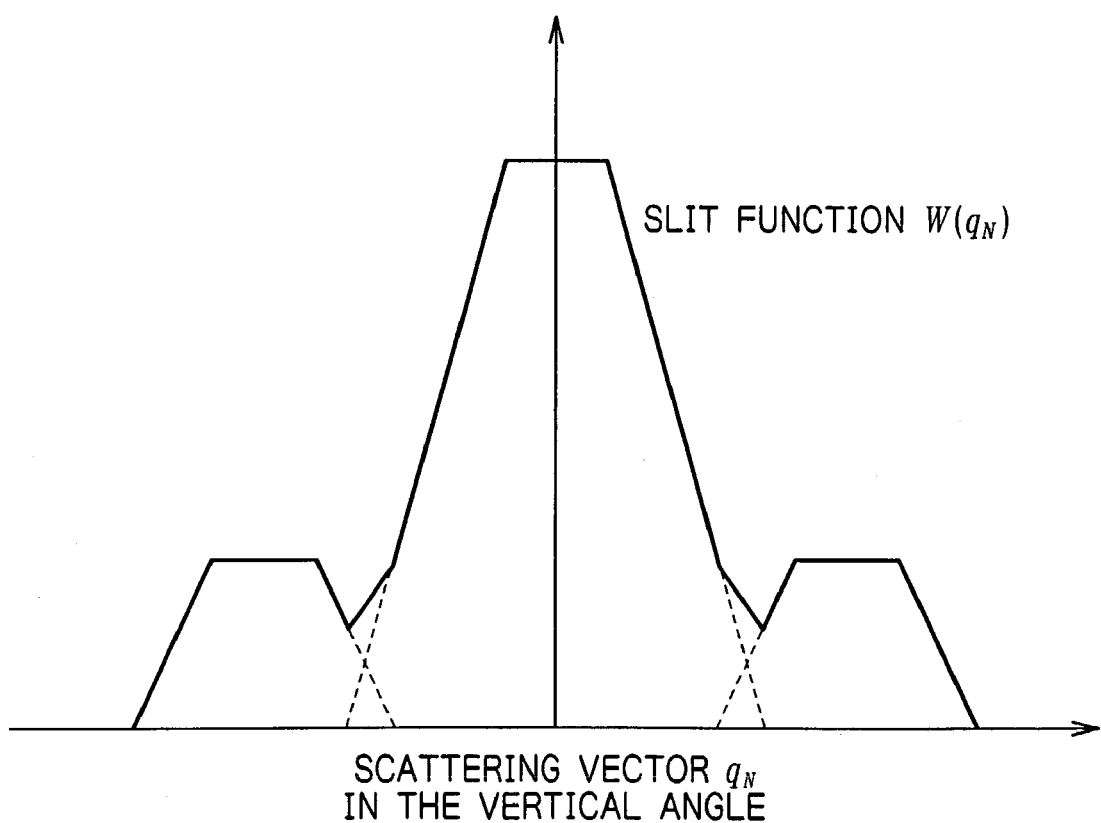
FIG. 24 is a graph showing the slit function obtained from the results shown in FIGS. 14D, 22D and 23D.

The X-ray measuring device 2 may have, for example, the structure illustrated in FIG. 6. As FIG. 6 shows, the X-ray measuring device 2 comprises an incident optical system 7 and a receiving side optical system 8. The incident optical system 7 applies X-rays, or propagation rays, to a sample 6. The receiving side optical system 8 detects the X-rays diverging from the sample 6. The incident optical system 7 has an X-ray source 9, a parabolic mirror 11, a first slit S1, and a second slit S2. The x-ray source 9 emits X-rays. The parabolic mirror 11 collimates X-rays emitted from the X-ray source 9 to 2θ rotation direction. The first slit S1 is provided on the optical path of the X-rays. The second slit S2 is provided on the optical path of the X-rays, too, and is located downstream with respect to the first slit S1.

The receiving side optical system 8 has a third slit S3, a fourth slit S4, and an X-ray detector 13. The third slit S3 is provided on the optical path of the X-rays. The fourth slit S4 is provided on the optical path of the X-rays, too, and is located downstream with respect to the third slit S3. The X-ray detector 13 is positioned downstream with respect to the fourth slit S4. The detector 13 is, for example, an SC (i.e., Scintillation Counter). As is knows in the art, the SC 13 is a so-called $0^{th}$ order counter that can receive X-rays in a point region.

The plane that is parallel to the plane of FIG. 6 and contains the X-ray axis X0 extending from the X-ray source 9 to the X-ray detecting point of the X-ray detector 13 is called "diffraction plane" or "scattering plane." The receiving side optical system 8 can rotate in the diffraction plane, around an axis X1 that passes through the sample 6 and extends perpendicular to the plane of FIG. 6. The rotation of the system 8 is generally known as "2θ rotation."

The X-ray source 9 incorporated in the incident optical system 7 has a filament (not shown) and a target (not shown). The filament emits thermoelectrons when supplied with a current. The target is arranged, opposing the filament. The thermoelectrons emitted from the filament impinge on a surface region of the target. This region is the X-ray focus, from which X-rays are radiated. The surface region of the target, on which the electrons impinge, is made of Cu (i.e., copper), Mo (i.e., molybdenum) or the like. In the case where the surface region is made of Cu, the target emits CuKα rays that are intense X-rays. The CuKα rays are mainly used as measuring X-rays.

The parabolic mirror 11 has a parabolic surface to which the X-rays are applied from the X-ray source 9. The X-ray source 9 is positioned at the geometrical focus of the parabolic surface of the mirror 11. The parabolic surface reflects the X-rays that diverge as they propagate from the X-ray source 9. Thus reflected, the X-rays are controlled in terms of their diversion and made into almost parallel X-ray beams. Nonetheless, the X-rays are parallel in the diffraction plane, that is, parallel to a plane parallel to the plane of FIG. 6. They have components that diverge in the plane, i.e., vertical diversion plane, which is perpendicular to the diffraction plane.

The parabolic surface region of the parabolic mirror 11 may be made of material that can reflect X-rays. Alternatively, it may be a multi-layered structure that comprises films of different materials, one laid upon another. If the parabolic surface region is a multi-layered structure, it can diffract specific X-rays, such as CuKα rays, with high efficiency, thanks to the periodicity of the multi-layered structure. Hence, the parabolic surface region can intensify the X-rays as the mirror 11 reflects the X-rays.

The first slit S1 and the second slit S2 constitute a so-called double-slit collimator 12. Thus, the slits S1 and S2 convert the X-rays coming from the parabolic mirror 11 into X-ray beams that have a smaller diameter and are more parallel than the X-rays. The parallel X-ray beams thus obtained are applied to a prescribed part of the sample 6.

When the X-rays are irradiated to the sample 6, the sample 6 emits scattered rays as re-diverging rays into a small-angle region that extends in the 2θ direction. Some of the scattered rays pass through the third slit S3 and are detected by the X-ray detector 13. The X-ray detector 13 counts the scattered rays and generates a signal whose magnitude corresponds to the intensity of the scattered rays.

The signal is output from the output terminal of the X-ray detector 13. The fourth slit S4 prevents the unnecessary scattered rays and other rays, which are generated at the third slit S3, from reaching the X-ray detector 13.

The X-ray detector 13 rotates in the diffraction plane, around the axis X1 of the sample 6. That is, the detector 13 undergoes a so-called "2θ rotation." While rotating so, the detector 13 counts the scattered rays and the like generated at the sample 6 and traveling in various directions that fall within the angle 2θ. As a result, the X-ray detector 13 generates count data representing the positions of the scattered rays traveling in said various directions.

The count data is transferred from the X-ray detector 13 to the signal-processing device 3 shown in FIG. 1. As FIG. 1 shows, the device 3 comprises a data-processing means 16, a slit-function output means 17, a model-function output means 18, an $I_{calc}$-calculating means 19, and a comparing means 21. The data-processing means 16 is connected to the X-ray detector 13 (see FIG. 6) arranged in the X-ray measuring device 2. The slit-function output means 17 generates a slit function $W(q_N)$ and outputs the same. The model-function output means 18 outputs a model function $I_{model}$. The $I_{calc}$-calculating means 19 calculates an $I_{calc}$.

Figure 3:
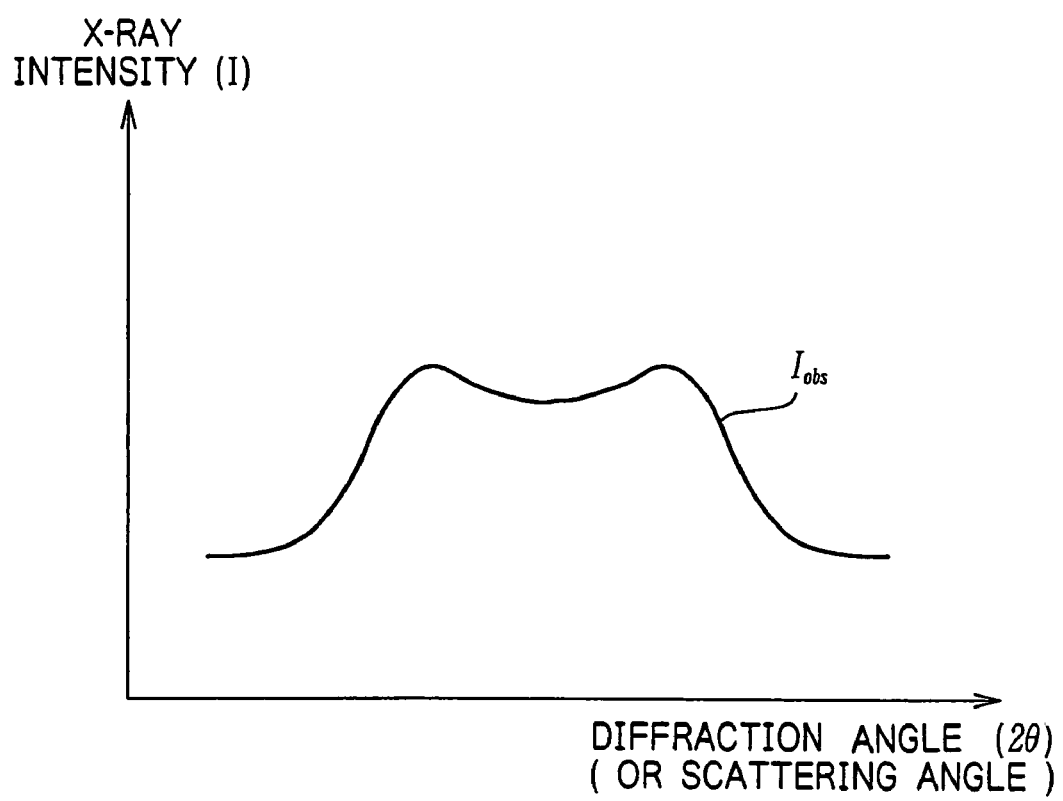
FIG. 3 is a graph schematically representing the measuring results obtained by the X-ray measuring device and the measured-data processing means, both illustrated in FIG. 1.
Figure 4:
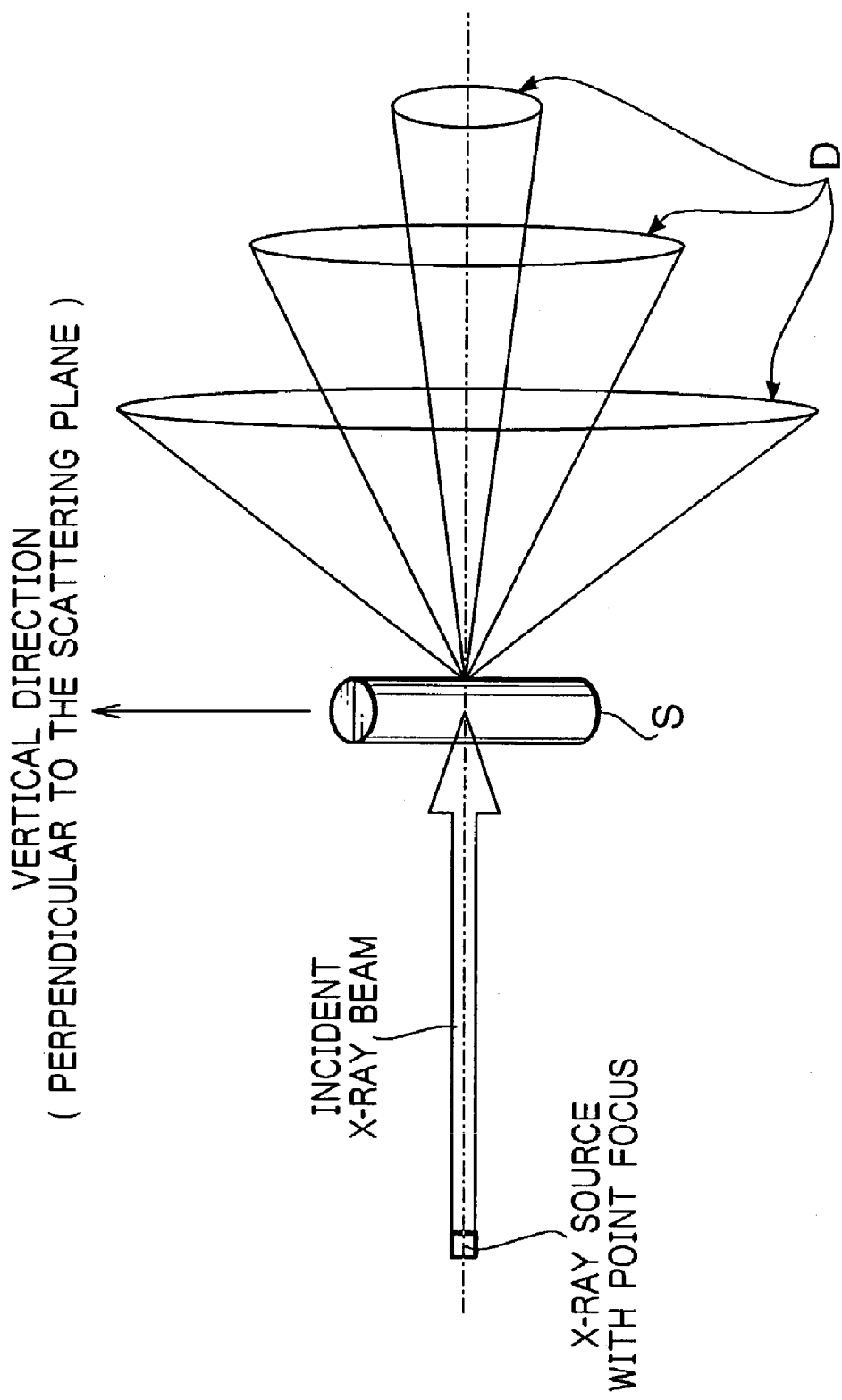
FIG. 4 is a diagram depicting an X-ray optical system, for explaining umbrella effect.
Figure 5:
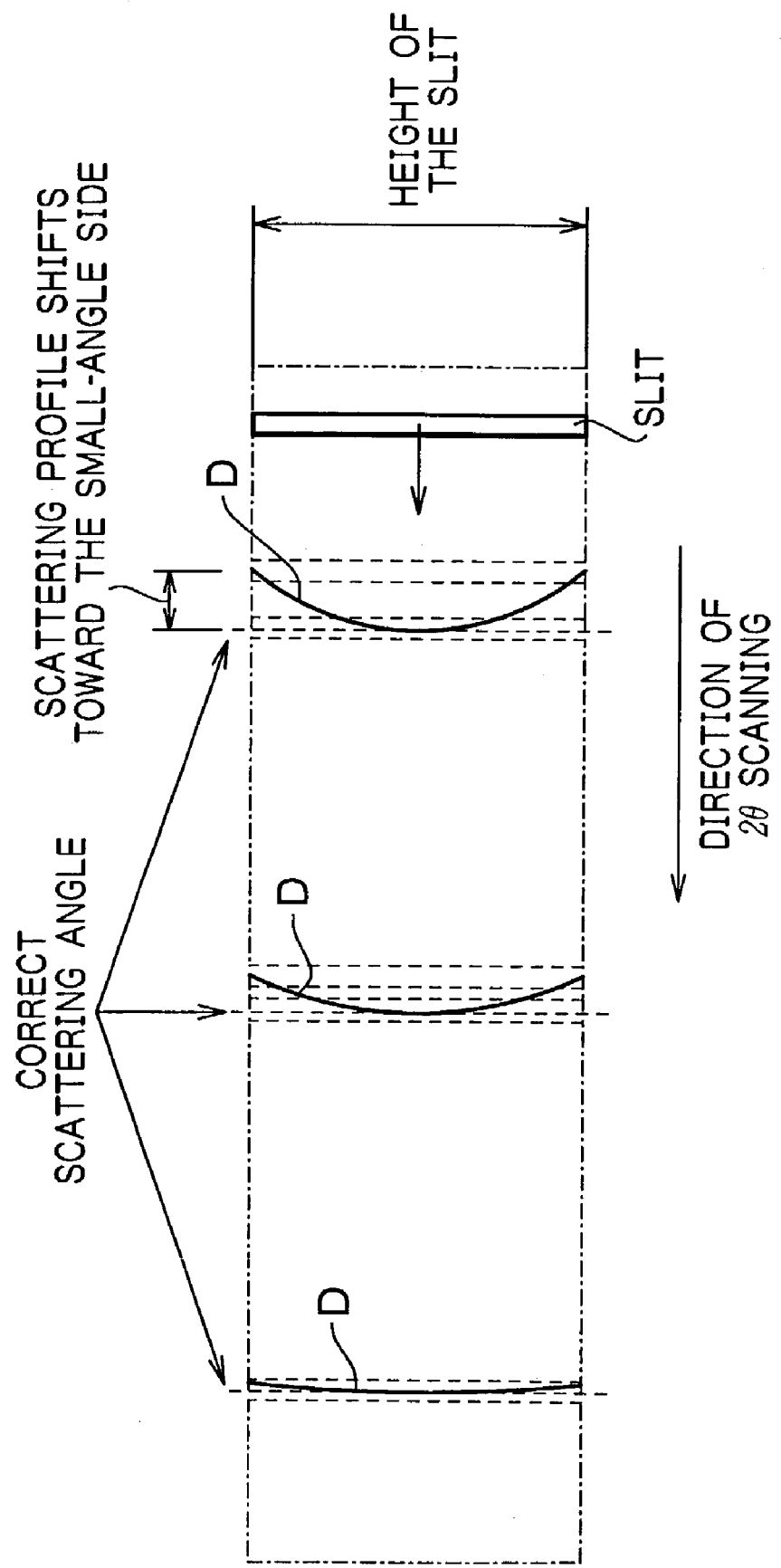
FIG. 5 is a diagram illustrating the relation between a slit and a Debye ring, for explaining umbrella effect.

The data-processing means 16 calculates a scattering profile from the signal output from the X-ray detector 13 that is provided in the X-ray measuring device 2. The scattering profile is, for example, the curve $I_{obs}$ shown in FIG. 3. It is a function that indicates the change that the intensity I of the scattered rays undergoes as the scattering angle 2θ, i.e., a variable, changes. In FIG. 3, the curve $I_{obs}$ is schematically shown for the sake of simplicity. It does not depict the actual results of measuring.

Figure 25:
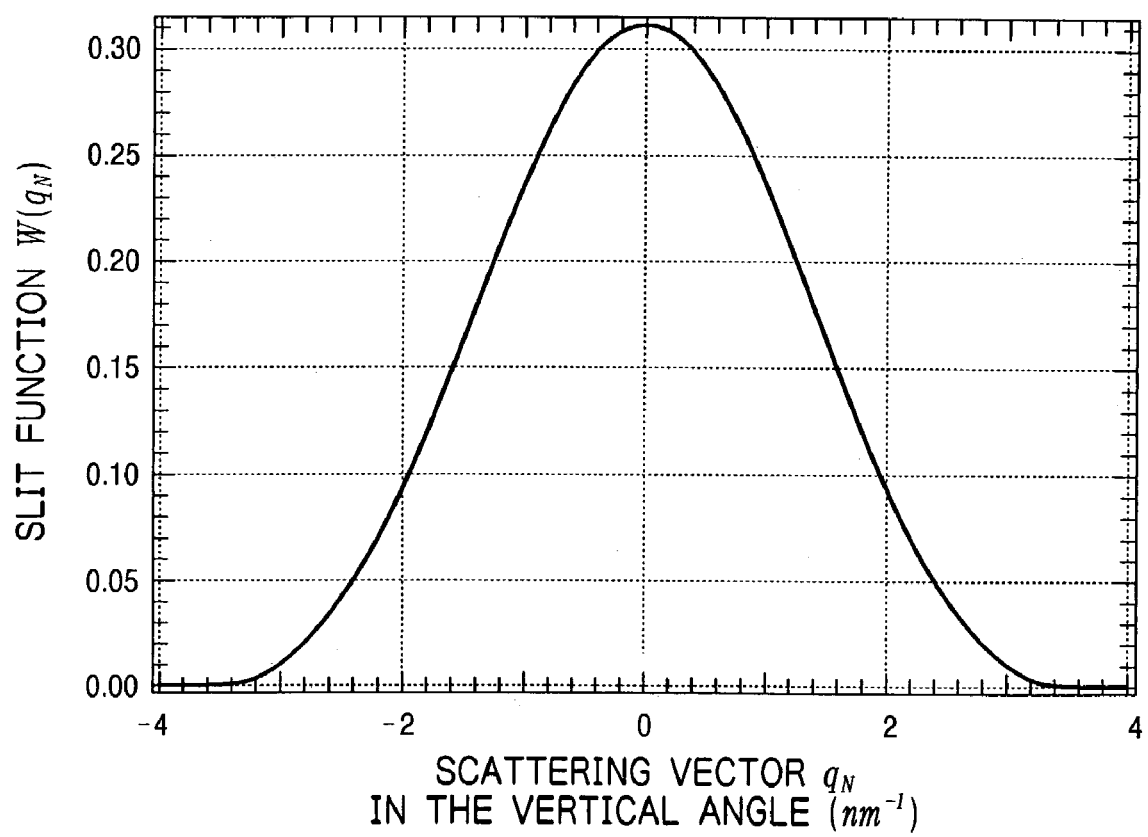
FIG. 25 is a graph depicting a slit function developed from the slit function shown in FIG. 24.

The slit-function output means 17 is a function element that generates and outputs, for example, the slit function $W(q_N)$ illustrated in FIG. 25. The slit function $W(q_N)$ may be generated as described above, with reference to FIGS. 4 to 24. It is desired that the slit-function output means 17 should include a storage means for storing the slit function $W(q_N)$ that the means 17 has generated. The storage means may store the function in the form of a mathematical formula or a data table showing the scattering vector $q_N$ and the slit function $W(q_N)$, both illustrated in FIG. 25.

To enable the slit-function output means 17 to generate the slit function $W(q_N)$, it is necessary to input to the means 17 various parameters concerning the X-ray measuring device 2 shown in FIG. 6. Among these parameters are filament size, slit height and inter-slit distance. An operator may input the parameters to the means 17, by using an input device such as a keyboard.

The slit-function output means 17 may not have the function of calculating the slit function $W(q_N)$. Rather, it may be one that performs only the function of store the slit function $W(q_N)$ generated by another function means.

The scattering profile shown in FIG. 3, actually acquired, is one generated as the true scattering profile $I_{true}$ changes due to, for example, umbrella effect. The model-function output means 18 shown in FIG. 1 is a function element that generates and outputs a model function $I_{model}$. The model function $I_{model}$ is a function that predicts the true scattering profile $I_{true}$, by using appropriate physical quantities as parameters. The model function $I_{model}$ can be set in various ways, either empirically or theoretically, in accordance with the structure of the optical system, which is the object to be measured.

The $I_{calc}$-calculating means 19 substitutes specific numerical values for the parameters contained in the model function $I_{model}$, thereby designating the model function $I_{model}$. The means 19 also substitutes a particular function value in the right side of the equation (3) set forth above, namely:

$$I_{obs}(q_N)=\int_{-\infty}^{\infty} W(q_N) \cdot I_{true}(\sqrt{(q_H^2+q_N^2)})dq_N$$

Thus, the $I_{calc}$-calculating means 19 determines value $I_{calc}$ that $I_{obs}$ ($q_N$) should have.

More specifically, the $I_{calc}$-calculating means 19 substitutes the slit function $W(q_N)$ generated by the slit-function output means 17, for $W(q_N)$ in the right side of the equation (3). Further, the means 19 substitutes the model function $I_{model}$, i.e., generated by applying specific numerical values as parameters, for the term $I_{true}$ ($\sqrt{(q_H^2+q_N^2)}$), thereby obtaining $I_{obs}(q_N)$. $I_{obs}(q_N)$, thus obtained, is used as $I_{calc}$.

The comparing means 21 compares the scattering profile data $I_{obs}$ obtained by the data-processing means 16, with the scattering profile $I_{calc}$ obtained by the $I_{calc}$-calculating means 19. In other words, the comparing means 21 determines whether the data $I_{obs}$ coincides with the scattering profile $I_{calc}$. The result of the comparison is displayed by the output device 4. The output device 4 is, for example, a display that displays information in the form of images, or a printer that prints information on recording media such as paper sheets.

The signal-processing device 3 shown in FIG. 1 comprises, for example, a computer that operates by a program. Like any other computer, this computer comprises an operation unit, a control unit, a storage unit, and the like. The operation unit and control unit comprise data-processing units such as CPUs (i.e., Central Processing Units) as in most computers. The storage unit comprises internal memories such as ROMs (i.e., Read Only Memories) and RAMs (i.e., Random Access Memories), as in most computers. External memories, such as a hard disk drive, a CD-ROM drive and a magneto-optical disk drive may be connected to the computer, if necessary. Further, input devices such as a keyboard and a mouse and output devices such as a display and a printer may be connected to the computer, if necessary.

The data-processing means 16, slit-function output means 17, model-function output means 18, $I_{calc}$-calculating means 19 and comparing means 21, all illustrated in FIG. 1, are each constituted by a computer program (i.e., software) and a computer that operates in accordance with the software. In some cases, each of these means may comprise hardware pieces such as logic circuits.

Figure 2:
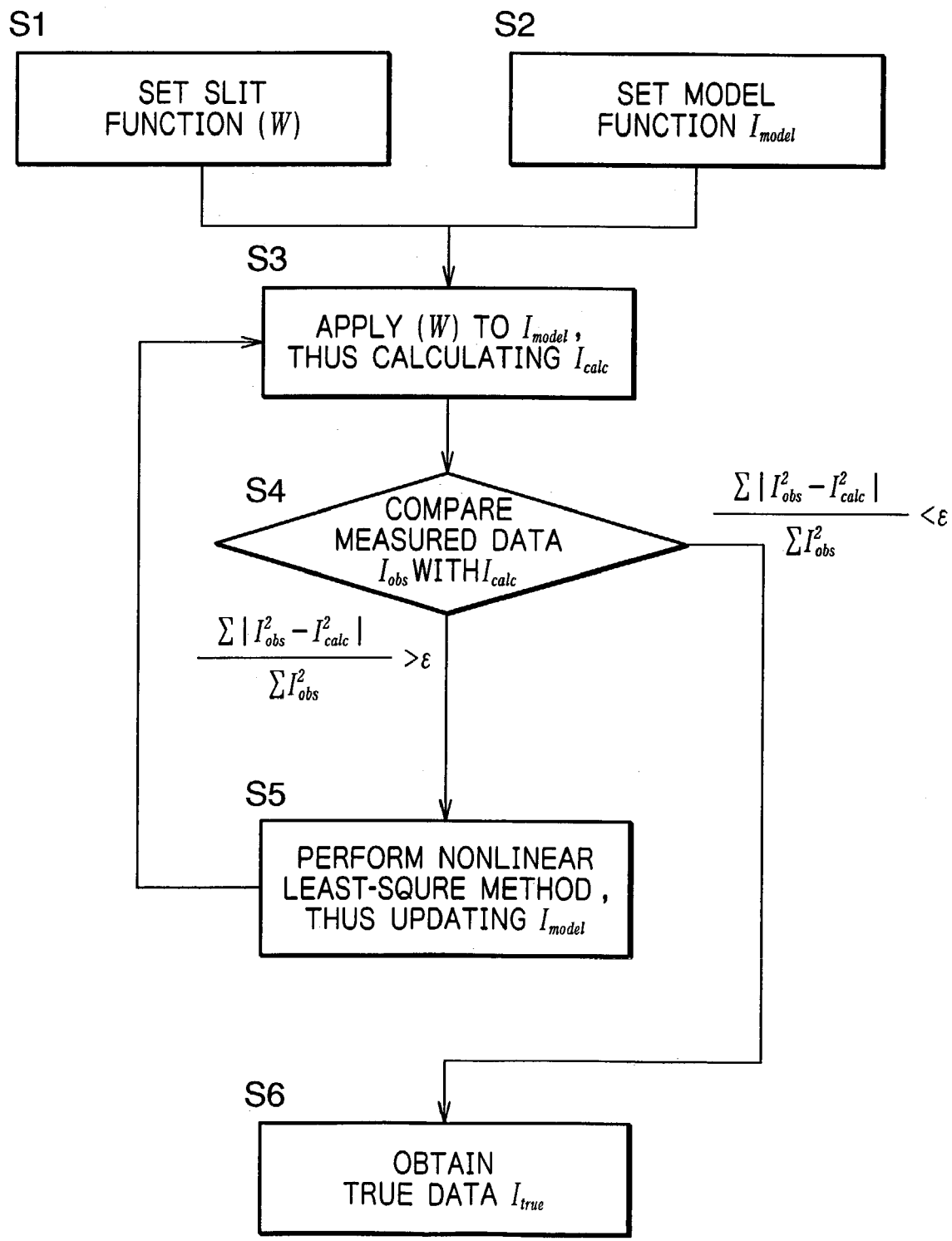
FIG. 2 is a flowchart for explaining a sample-analyzing method which is performed by the apparatus shown in FIG. 1.

FIG. 2 is a flowchart that explains various controls performed by the signal-processing device 3 shown in FIG. 1. With reference to the flowchart, how the signal-processing device 3 operates will be described.

In Step S1, the slit-function output means 17 of the signal-processing device 3 sets the slit function $W(q_N)$ in the form of such a curve as shown in FIG. 25. The slit function $W(q_N)$ is stored as, for example, a data table in, for example, a RAM or any other appropriate storage medium.

Meanwhile, in Step S2, the model-function output means 18 of the signal-processing device 3 sets a model function $I_{model}$. The model function $I_{model}$ is a function that has been approximated to $I_{true}$ ($\sqrt{(q_H^2+q_N^2)}$) in the right side of the equation (3), by applying appropriate parameters. Recall that the equation (3) reads as follows:

$$I_{obs}(q_N)=\int_{-\infty}^{\infty} W(q_N) \cdot I_{true}(\sqrt{(q_H^2+q_N^2)})dq_N \quad (3)$$

The model-function output means 18 sets a model function for itself. It also substitutes specific values for the parameters contained in the model function, thereby determining the model function $I_{model}$.

In Step S3, the $I_{calc}$-calculating means 19 of the signal-processing device 3 substitutes the slit function $W(q_N)$ and the model function $I_{model}$, which have been set in Steps S1 and S2, respectively, in the right side of the equation (3). Thus, the $I_{calc}$-calculating means 19 calculates a scattering function $I_{calc}(q_N)$.

In Step S4, the comparing means 21 of the signal-processing device 3 determines whether the scattering function $I_{obs}$ actually obtained by the data-processing means 16 coincides with the scattering function $I_{calc}$ calculated in Step S3 by using the slit function $W(q_N)$. For example, the device 3 determines whether value $A$, given by the following equation (5), is smaller than convergence value $\epsilon$ or not.

$$A = \Sigma |I\ obs^2 - I\ calc^2| / \Sigma\ I\ obs^2 \qquad (5)$$

More precisely, if value $A$ is smaller than value $\epsilon$, the device 3 determines that the scattering function $I_{obs}$ actually obtained coincides with the scattering function $I_{calc}$ calculated in Step S3. In this case, the device 3 determines in Step S6 that the scattering function $I_{obs}$ actually obtained is the true scattering function $I_{true}$.

The true scattering function $I_{true}$ is a function that has been determined by applying the slit function $W(q_N)$ as seen from the equation (3). Hence, the function $I_{true}$ represents a reliable and correct scattering profile free of measuring errors that may result from the umbrella effect when slits are employed.

In Step S4, the comparing means 21 may determine that value $A$ is larger than value $\epsilon$. If this is the case, the scattering function $I_{obs}$ actually obtained is determined not to coincide with the scattering function $I_{calc}$ calculated. In other words, the scattering function $I_{obs}$ actually obtained is found not to pertain to the true scattering function $I_{true}$. In this case, the parameters in the model function $I_{model}$ are updated by the use of nonlinear least-square method.

Next, the control flow returns to Step S3. In Step S3, $I_{calc}$ is calculated again, for the model function $I_{model}$ that contains parameters updated. Then, in Step S4, the comparing means 21 compares $I_{calc}$ with the measured data $I_{obs}$. Steps S3, S4 and S5 are repeated until the value $A$ of the equation (5) becomes smaller than the convergence value $\epsilon$. When the value $A$ becomes smaller than the value $\epsilon$, the true scattering function $I_{true}$ is finally obtained. An ideal convergence value $\epsilon$ is 0(zero). In practice, however, $\epsilon$ is set at a small value ranging, for example, from $10^{-5}$ to $10^{-10}$.

As indicated above, in the method and apparatus for analyzing samples by using X-rays, both according to the present embodiment, the re-reflection of X-rays from the sample and the X-ray irradiating positions in the lengthwise direction of the sample are taken into account, thereby calculating the slit function $W(q_N)$. The slit function $W(q_N)$ thus calculated is therefore far more correct and reliable than the slit function $W$ obtained in the conventional method. Note that, in the conventional method, the function $W(q_N)$ is determined based on only the divergence of X-rays applied to the sample.

In most conventional sample-analyzing methods, the true function $I_{true}$ is calculated from the function $I_{obs}$ actually acquired and the slit function $W$. Hence, the conventional methods can hardly calculate the true function $I_{true}$ if the slit function $W$ is complex and complicated. In the method according to this embodiment of the present invention, the nonlinear least-square method is performed, approximating model function $I_{model}$ toward the function $I_{obs}$ actually acquired. The function $I_{true}$ can therefore be obtained without fail.

In the sample-analyzing method according to this embodiment, the model function $I_{model}$ and the slit function $W$ can be set at any desired values in accordance with the structure of the optical system, which is the object of analysis.

(Second Embodiment)

Figure 26:
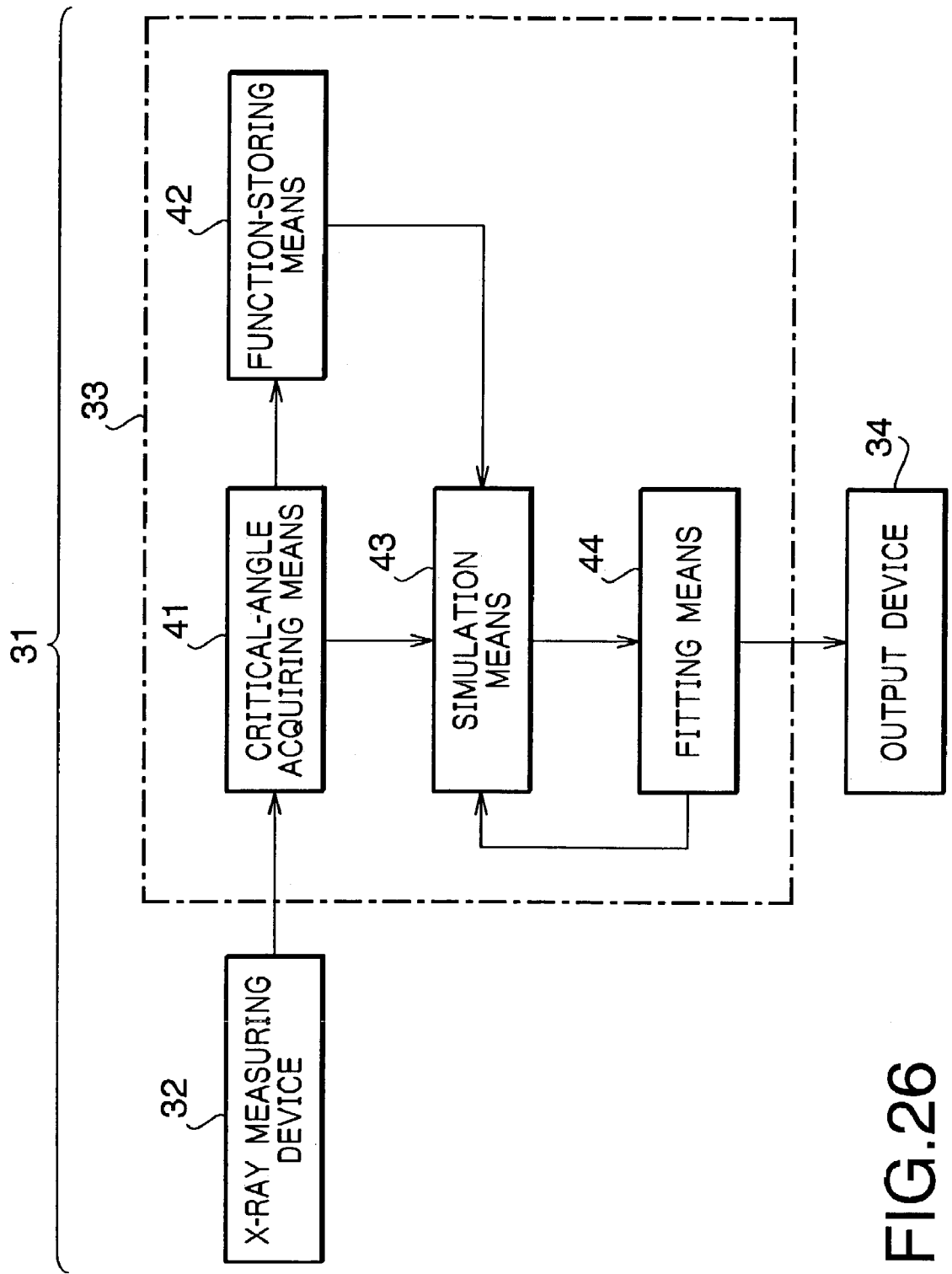
FIG. 26 is another embodiment of a block diagram of a sample-analyzing apparatus according to the present invention.

An embodiment of the invention will be described, which are a method and apparatus for analyzing a sample by applying X-rays to determine the density non-uniformity of the sample in which particles are dispersed not uniformly. FIG. 26 is a block diagram illustrating the sample-analyzing apparatus. The second embodiment is designed to analyze the average size of the particles and the distribution of particle size, both impairing the density uniformity of the sample.

A sample-analyzing apparatus 31 has an X-ray measuring device 32, a signal-processing device 33, and an output device 34. The X-ray measuring device 32 applies X-rays to the sample, thereby obtaining an X-ray reflectivity curve and an X-ray scattering curve, both pertaining to the sample. The sample may be a thin film. In this case, the goniometer provided in the X-ray measuring device 32 supports the sample and measures the X-ray reflectivity curve and X-ray scattering curve, while controlling the X-ray incidence angle $\theta_{in}$, X-ray exit angle $\theta_{out}$ and scattering angle $2\theta = \theta_{in} + \theta_{out}$.

The reflectivity curve is obtained under the condition of: $\theta_{in} = \theta_{out}$. The scattering curve is obtained under the conditions of: $\theta_{in} = \theta_{out} \pm \Delta\omega$; $\theta_{in}$ is constant, and $\theta_{out}$ is scanned, or under the conditions of: $\theta_{in} = \theta_{out} \pm \Delta\omega$; $\theta_{out}$ is constant, and $\theta_{in}$ is scanned. The signal-processing device 33 has a critical-angle acquiring means 41, a function storing means 42, a simulation means 43, and a fitting means 44. The critical-angle acquiring means 41 acquires a critical angle $\theta c$ from the X-ray reflectivity curve and the X-ray scattering curve, both having obtained by the X-ray measuring device 32.

The critical angle $\theta c$ is an element of the scattering function, on the basis of which the signal-processing device 33 carries out processes. The critical angle $\theta c$ can be determined from the X-ray reflectivity curve by means of the method known in the art. For instance, the angle at which the reflectivity (i.e., intensity of the X-rays reflected) abruptly decreases may be regarded as critical angle $\theta c$. Note that the critical angle $\theta c$ has the following relation with the refractive index n:

$$\theta c = \sqrt{(2\ \delta)}$$

$$n = 1 - \delta$$

Therefore, value $\delta$ may be calculated from the critical angle $\theta c$.

The function-storing means 42 stores the scattering function and some other functions, all being utilized to analyze the sample. The simulation means 43 calculates a simulated X-ray scattering curve, by using either $\theta c$ or $\delta$ and by selecting an appropriate value for the fitting parameter contained in the scattering function. The scattering function and other functions, which are used to analyze the sample, may be one expressed by the following equations (1) to (6):

$$\delta = \frac{r_e}{2\pi} \lambda^2 N_A \cdot \rho \cdot \frac{\sum_j c_j \mathrm{Re}(f_j)}{\sum_j c_j M_j} \qquad \text{Equation (1)}$$

$r_e$: classical electron radius $\cong 2.818 \times 10^{-13}$ cm $N_A$: Avogadro's constant $\cong 6.022 \times 10^{23}$ mol$^{-1}$ $\rho$: average density of the sample having non-uniform density $c_j$: composition ratio of the elements $j$ in the sample having non-uniform density $M_j$: mass number of the elements $j$ in the sample having non-uniform density $f_j$: atomic scattering factor of the elements $j$ in the sample having non-uniform density $$I(\theta_{in}, \theta_{out}) = \int \left| F_S\left(\sqrt{q_H^2 + q_N^2}\,; \{p\}\right)\right|^2 P(\{p\})d\{p\} \qquad \text{Equation (2)}$$

$$q = \frac{4\pi \sin\left(\frac{\sqrt{\theta_{in}^2 - 2\delta} + \sqrt{\theta_{out}^2 - 2\delta}}{2}\right)}{\lambda}$$

$I(\theta_{in}, \theta_{out})$: scattering function $F_S\left(\sqrt{q_H^2 + q_N^2}\,; \{p\}\right)$: scattering form-factor causing the non-uniform density $q = |q|$: magnitude of scattering vector $q$: scattering vector $\theta_c = \sqrt{2\delta}$: critical angle $n = 1 - \delta$: refractive index $\lambda$: wavelength of x-ray $P(\{p\})d\{p\}$: scattering function defining the non-uniform density $\{p\}$: set of parameters of scattering functions $$I\left(\sqrt{q_H^2 + q_N^2}\right) = \int_0^\infty dR \cdot |\Omega^{FT}\left(\left(\sqrt{q_H^2 + q_N^2}\right), R\right)|^2 \cdot P_{R_0}^M(R) \cdot \frac{1}{R^3} R_0^3 \rho_0 \cdot W(q_N) \qquad \text{Equation (3)}$$

$P_{R_0}^M(R)$: particle-diameter distribution function $R_0$: average size parameter of particles $M$: distribution broadening parameter of particles $R$: integral variable $q = |q|$: magnitude of scattering vector $q$: scattering vector $\rho_0$: average density of particles $\Omega^{FT}\left(\left(\sqrt{q_H^2 + q_N^2}\right), R\right)$: particle form-factor $W(q_N)$: slit function $$P_{R_0}^M(R) = \frac{\left(\frac{M}{R_0}\right)^M}{\Gamma(M)} \cdot e^{\frac{MR}{R_0}} \cdot R^{M-1}$$

Equation (4)

$\Gamma(M)$: $\Gamma$ function $$\Omega^{FT}\left(\left(\sqrt{q_H^2 + q_N^2}\right), R\right) = \frac{4\pi R^3}{\left(\sqrt{q_H^2 + q_N^2} \cdot R\right)^3}\left[\sin\left(\sqrt{q_H^2 + q_N^2} \cdot R\right) - \left(\sqrt{q_H^2 + q_N^2} \cdot R\right) \cdot \cos\left(\sqrt{q_H^2 + q_N^2} \cdot R\right)\right]$$

Equation (5)

$$I\left(\sqrt{q_H^2 + q_N^2}\right) = \frac{8\pi^2\left(1 + \frac{4\sqrt{q_H^2+q_N^2}^2 R_0^2}{M^2}\right)^{-\frac{-1+M}{2}}}{(-3+M)(-2+M)(-1+M)\sqrt{q_H^2+q_N^2}^6} \times W(q_N) \times$$

$$\left\{ M^3\left(1 + \frac{4\sqrt{q_H^2+q_N^2}^2 R_0^2}{M^2}\right)\left[\left(1 + \frac{4\sqrt{q_H^2+q_N^2}^2 R_0^2}{M^2}\right)^{\frac{-3+M}{2}} - \cos\left[(-3+M)\tan^{-1}\left(\frac{2\sqrt{q_H^2+q_N^2} R_0}{M}\right)\right]\right] + \right.$$

$$(-3+M)(-2+M)M \cdot \sqrt{q_H^2+q_N^2}^2 \cdot R_0^2\left[\left(1 + \left(\frac{4\sqrt{q_H^2+q_N^2}^2 R_0^2}{M^2}\right)\right)^{\frac{-1+M}{2}} + \cos\left[(-1+M)\tan^{-1}\left(\frac{2\sqrt{q_H^2+q_N^2} R_0}{M}\right)\right]\right] -$$

$$\left. 2(-3+M)M^2 \cdot \sqrt{q_H^2+q_N^2} \cdot R_0\left(1 + \frac{4\sqrt{q_H^2+q_N^2}^2 R_0^2}{M^2}\right)^{\frac{1}{2}} \sin\left[(-2+M)\tan^{-1}\left(\frac{2\sqrt{q_H^2+q_N^2} R_0}{M}\right)\right]\right\}$$

Equation (6)

The fitting means 44 shown in FIG. 26 achieves fitting on the X-ray scattering curve simulated by the simulation means 43 and the X-ray scattering curve actually obtained by the X-ray measuring device 32. The data items required for the simulation and the fitting, such as the X-ray reflectivity curve measured, X-ray scattering curve measured, X-ray incident angle $\theta_{in}$ and X-ray exit angle $\theta_{out}$, should better be automatically supplied from the X-ray measuring device 32 to the signal-processing device 33. More specifically, it is desired that they should be automatically sent to the critical angle-acquiring means 41, simulation means 43 and fitting means 44. These data items can, of course, be manually input.

To apply Equations (1) to (6) to simulate the X-ray scattering curve, the simulation means 43 requires $\theta c$ (or $\delta$), $\theta_{in}$, $\theta_{out}$, $\lambda$, $\mu$, d, $\rho_0$ and the like. Thus, the X-ray measuring device 32 automatically supplies, for example, $\theta_{in}$ and $\theta_{out}$, (or $2\theta$). Values $\lambda$, $\mu$, d, $\rho_0$ are manually input, stored in advance, or calculated. The sample-analyzing apparatus 31 or the signal-processing device 33 therefore needs to have input means, storage means or calculation means. Needless to say, these means and the simulation means 43 are configured to receive and transmit data.

The signal-processing device 33 repeatedly simulates the X-ray scattering curve as the simulation means 43 changes the fitting parameter, until the fitting means 44 determines that the X-ray scattering curve simulated coincides with the X-ray scattering curve actually obtained. The value that the fitting parameter has when both curves coincide with each other is regarded as indicating the actual distribution of particles. This value is, for example, the average size of the particles and the distribution broadening of particles. The output device 34 presents the results of this analysis in the form of visual data, such as an image displayed on a display screen or printed on a printing media, e.g., paper sheet.

The results of analysis, obtained by the sample-analyzing apparatus 31, more precisely, the signal-processing device 33 may be utilized in manufacturing thin films. If this is the case, they are transmitted directly to the thin-film manufacturing apparatus or the apparatus that controls the thin-film manufacturing apparatus.

The signal-processing device 33 shown in FIG. 26 is, for example, a computer program, i.e., software and a computer that operates in accordance with the software. In some cases, the means incorporated in the device 33 may comprise hardware pieces such as logic circuits.

To automatically select an optimal fitting parameter that the simulation means 43 uses, least-square method may be employed to raise the probability that the simulated and measured curves coincide with each other. That is, the signal-processing device 33 may incorporate a computer or the like that can automatically select an optimal fitting parameter. The optimal fitting parameter can, of course, be manually input.

Figure 27:
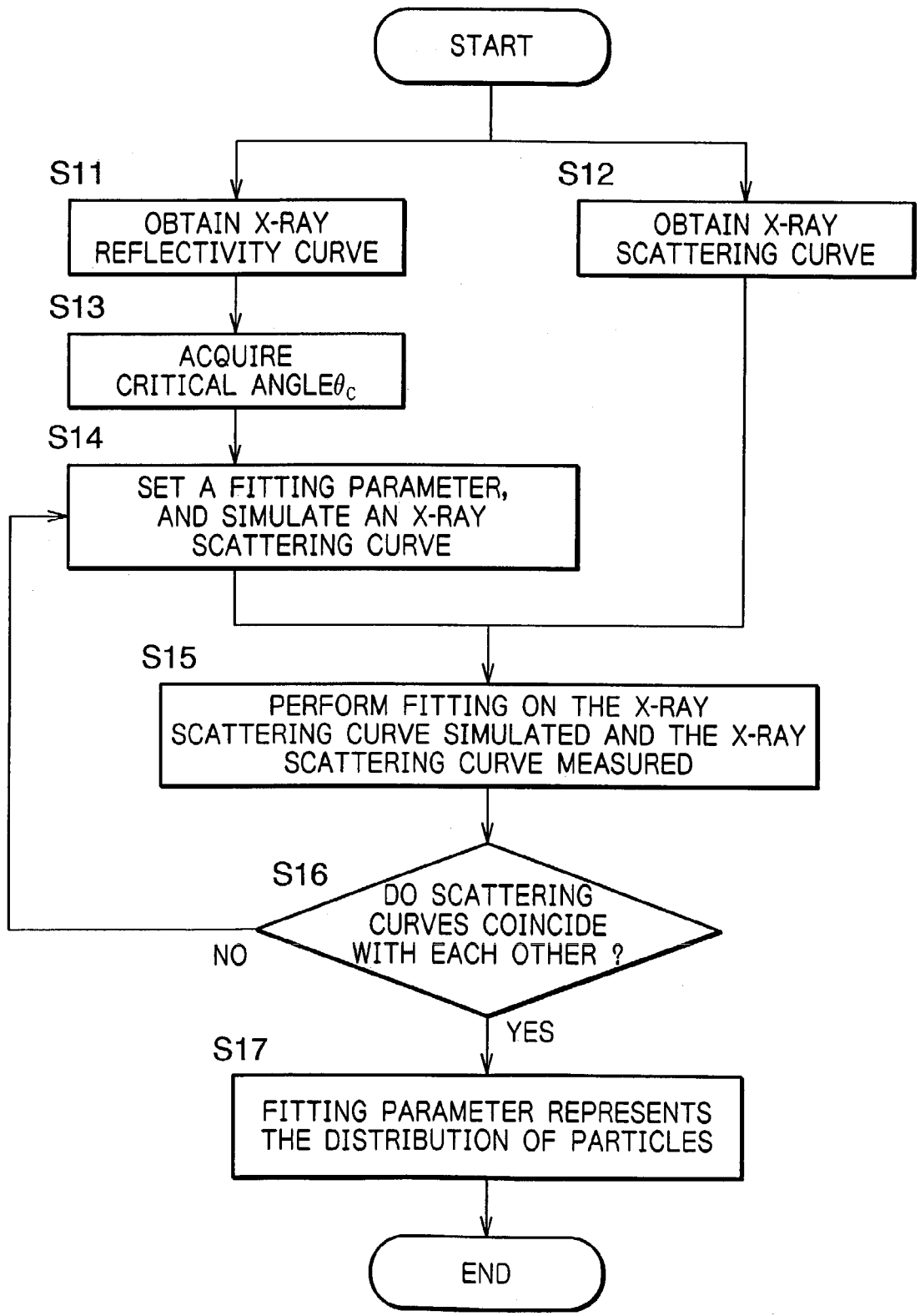
FIG. 27 is a flowchart for explaining a sample-analyzing method, which is performed by the apparatus shown in FIG. 26.

FIG. 27 is a flowchart explaining a sample-analyzing method that the apparatus 31 of FIG. 26 may perform. This sample-analyzing method is designed to analyze samples, such as thin films and bulk bodies, in which particles are dispersed not uniformly. The method uses the fitting parameter that represents the distribution of particles in the sample, thereby setting a scattering function equivalent to an X-ray scattering curve. The method applies the scattering function to simulate an X-ray scattering curve pertaining to the sample.

Figure 28A:
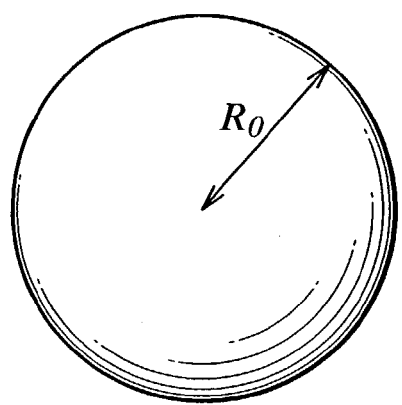
FIGS. 28A and 28B show two models of particles, respectively, which are used in the sample-analyzing method of FIG. 27, the first model being spherical and the second being cylindrical.
Figure 28B:
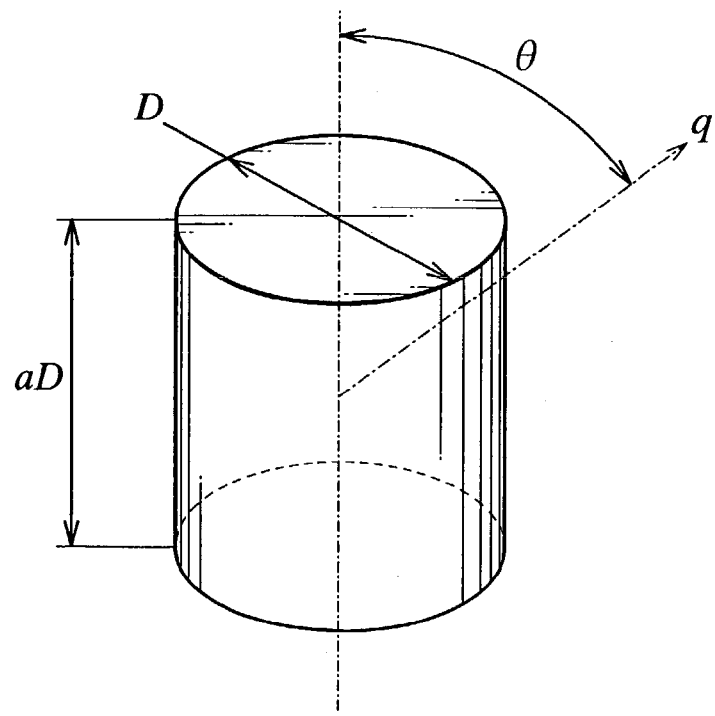

The scattering function may be one selected from the following functions:

(1) A function using fitting parameters "$R_0$" and "M" which indicate, respectively, the average size and distribution broadening of particles of such a spherical model as illustrated in FIG. 28A;

(2) A function using fitting parameters "D" and "a" which indicate, respectively, the diameter and aspect ratio of particles of such a cylindrical model as depicted in FIG. 28B;

(3) A function using fitting parameter "L" which indicates the minimum inter-particle distance and fitting parameter "η" which indicates the inter-particle correlation coefficient; or (4) A function using fitting parameter "P" which indicates the content of particles and fitting parameter "ε" which indicates the inter-particle distance, respectively.

Whichever scattering function is applied, both the X-ray reflectivity curve and the X-ray scattering curve are required, and various values derived from theses curves are indispensable. Therefore, before the simulation and fitting are carried out, an X-ray reflectivity curve concerning the sample, e.g., a thin film or a bulk body, is obtained in Step S11, and an X-ray scattering curve pertaining to the sample is obtained in Step S12.

In Step S11, the X-ray reflectivity curve is obtained under the condition of X-ray incident angle $\theta_{in}$=X-ray exit angle $\theta_{out}$. That is, the X-rays undergo specular reflection. The X-ray incident angle $\theta_{in}$ is the angle at which X-rays are applied to the surface of the sample that has non-uniform density. The X-ray exit angle $\theta_{out}$ is the angle at which the X-rays exit from the surface of the sample that has non-uniform density.

In Step S12, the X-ray scattering curve is obtained under the condition of $\theta_{in}=\theta_{out}-\Delta\omega$, Where $\theta_{in}$ is the X-ray incident angle, $\theta_{out}$ is the X-ray exit angle and $\Delta\omega$ a is the offset; under the condition of $\theta_{in}=\theta_{out}+\Delta\omega$, where $\theta_{in}$ is the X-ray incident angle, $\theta_{out}$ is the X-ray exit angle and $\Delta\omega$ is the offset; or under both conditions. Hereinafter, these conditions shall be generally referred to as "$\theta_{in}=\theta_{out}\pm\Delta\omega$."

Note that the offset $\Delta\omega$ is the angle difference between $\theta_{in}$ and $\theta_{out}$. Hence, $\theta_{in}=\theta_{out}$ if $\Delta\omega=0°$. In this case, the X-rays undergo specular reflection, and the X-ray reflectivity of the sample is measured. The X-ray scattering curve is obtained under the condition that the offset Δ107 is a little different from 0°. Namely, the X-ray scattering curve is obtained under the condition that the incident angle $\theta_{in}$ and the exit angle $\theta_{out}$ differ a little from each other. It is desired that the offset $\Delta\omega$ be as much close to 0° as possible so that the specular reflection occurring when $\Delta\omega=0°$ may least influence the measuring of the X-ray scattering curve.

To obtain an X-ray scattering curve obtained under the condition of $\theta_{in}=\theta_{out}\pm\Delta\omega$ is to measure the scattering of X-rays which has resulted from the particles existing in the thin film or bulk body, or from the non-uniform density of the sample. Hence, the non-uniform density of the thin film or bulk body can be reliably analyzed if the X-ray scattering curve actually obtained is fitted to an X-ray scattering curve simulated by using various functions as will be described later.

The X-ray scattering curve may be obtained by scanning the X-ray exit angle $\theta_{out}$, while maintaining the X-ray incident angle $\theta_{in}$ at a constant value. Alternatively, it may be obtained by scanning the X-ray incident angle $\theta_{in}$, while maintaining the X-ray exit angle $\theta_{out}$ at a constant value. In either case, it is possible to measure the X-ray diffusion and scattering reliably, in order to accomplish simulation and fitting at high precision.

The scattering function used to analyze the sample employs the critical angle θc of the sample that has a non-uniform density. Thus, the critical angle θc is determined directly from the X-ray reflectivity curve obtained in Step S11. The angle θc can be determined from the X-ray reflectivity curve by any known method. For example, the angle at which the reflectivity (i.e., intensity of the X-rays reflected) abruptly decreases, as seen from the X-ray reflectivity curve, is considered to be the critical angle θc. The critical angle θc has the following relations with the value d and the refractive index n:

$$\theta c = \sqrt{(2\ \delta)}$$

$$n = 1 - \delta$$

If the element that constitutes the sample having a non-uniform density is identified, it is possible to determine the average density ρ of the sample from the value δ. More precisely, the average density ρ of the sample can be determined by Equation (1) specified above, if the composition ratio $C_j$, mass number $M_j$ and atomic scattering factor $f_j$ of the element j are known.

The numerical values required to calculates the average density ρ can be inferred when the sample having a non-uniform density is prepared. The average density ρ of the sample, included in Equation (1), is information very useful in evaluating and preparing the sample, like the diameter and distribution broadening of the particles that exist in the sample, which are determined as will be described later.

Thus, preparations are made for the simulation and fitting as described above. Then, in Step S14, a scattering function that defines the X-ray scattering curve is set in accordance with the fitting parameters that represent the distribution of the particles. Further, values are selected for the fitting parameters, and an X-ray scattering curve is simulated under the same conditions the scattering curve has been actually obtained. That is, the curve is simulated by scanning $\theta_{out}$ in the equation, $\theta_{in}=\theta_{out}\pm\Delta\omega$, while maintaining $\theta_{in}$ at a constant value, or by scanning $\theta_{in}$ in the equation, $\theta_{in}=\theta_{out}\pm\Delta\omega$, while maintaining $\theta_{out}$ at a constant value.

To state it more precisely, a scattering function is first set, which is defined by Equation (2) set forth above. The scattering function thus set represents an X-ray scattering curve pertaining to all incident angles $\theta_{in}$ and all exit angles $\theta_{out}$, except for the case where $\theta_{in}=\theta_{out}$. In the scattering function given by Equation (2), the scattering form-factor causing the non-uniform density is an important element that defines the X-ray scattering curve.

The scattering form-factor causing the non-uniform density defines a shape model of the particles contained in the sample that has a non-uniform density. The factor indicates that particles of the shape model are distributed in a specific way in the sample. This factor helps to simulate an X-ray scattering curve accurately showing the influence of particle distribution, with a high degree of freedom and a high precision. Note that the scattering function {p} defining the non-uniform density may be one of parameter sets, each determining a scattering function.

The shape model of particles may be such a spherical model as shown in FIG. 28A or such a cylindrical model as illustrated in FIG. 28B. A shape model can be selected and applied in accordance with the sample to be analyzed. Hence, the shape of any particle in the sample can be modeled.

A scattering function $I(\sqrt{(q_H^2+q_N^2)})$ using the spherical model is defined by Equation (3). In Equation (3), the particle-diameter distribution function is given by Equation (4), and the particle form-factor defining the shape of particles is given by Equation (5). Equation (3) may be developed into, for example, Equation (6) by applying Equations (4) and (5).

In this case, the parameter "$R_0$" indicating the average size of the particles of spherical model and the parameter "M" indicating the distribution broadening of the particles are fitting parameters that represent the distribution of the particles. The scattering function $I(\sqrt{(q_H^2+q_N^2)})$ in Equations (3) and (6) can indicate various distributions of particles, if these fitting parameters [$R_0$, M] are changed. The scattering functions therefore defines the X-ray scattering curve that is influenced by the distribution of the particles. If the cylindrical model of FIG. 28B is utilized, the diameter "D" and aspect ratio "a" of the particles may be used as fitting parameters (aD).

The equation (4) set forth above expresses a gamma distribution, or the particle-size distribution. Needless to say, another particle-size distribution, such as a Gauss distribution, may be applied in the present embodiment. The best particle-size distribution available should be selected and applied in order to achieve a high-precision fitting of the simulated scattering curve and the measured scattering curve. If the cylindrical model is used for the particles, the scattering function disclosed in Japanese Unexamined Patent Publication No. 2001-349849 can be utilized.

The scattering vector q in each of the equations represents the refraction of X-rays which is caused by the particles. If the sample is a thin film, the refraction of the X-rays at the surface of the thin film imposes a great influence on the scattering curve actually obtained. The refraction of the X-rays must be taken into account in the process of simulating a scattering curve, so that the non-uniform density of the thin film is analyzed with high precision.

In this embodiment, the scattering vector q that represents the X-ray refraction defined by Equation (2) is applied as an optimal scattering function to simulate a scattering curve. Generally, the scattering vector q is given as follows:

$q=(4\pi \sin \theta\ s)/\lambda.$

In the case of a thin film, however, the angle $2\theta_s$ at which the X-rays are scattered by the particles has the following relation with the X-ray incident angle $\theta_{in}$ and X-ray exit angle $\theta_{out}$:

$$2\theta_s=\sqrt{(\theta out-2\delta)}+\sqrt{(\theta in-2\delta)} \qquad (6)$$

The angle $2\theta_s$ is therefore introduced into the general formula. The critical angle $\theta c$ acquired from the X-ray reflectivity curve is used in the scattering vector q. That is, $\theta c=\sqrt{(2\delta)}$.

As mentioned above, the scattering function defined by an equation selected from Equations (3) to (6) is applied to simulate various scattering curves that accord with the average particle-size parameter "$R_0$" and the distribution-broadening parameter "M," both being fitting parameters, in consideration of the influence imposed by the particles. Hence, the scattering curve simulated can be very similar to the scattering curve actually obtained, if the values for the parameters "$R_0$" and "M" are optimized.

The method of simulating the X-ray scattering curve by using the aforementioned scattering function will be further described. First, simulation conditions are set, which are just the same as the conditions of actually obtaining the scattering curve. The scattering function pertaining to the spherical model, i.e., Equation (3), (4), (5) or (6), may be selected. In this case, appropriate values are selected for the "$R_0$" and the distribution-broadening parameter "M." Then, the equation (6), again set forth below, is applied:

$$2\theta_s=\sqrt{(\theta out-2\delta)}+\sqrt{(\theta in-2\delta)}$$

Thus, an X-ray scattering curve is simulated by applying the fitting parameters [$R_0$, M] whose values have been selected by scanning $\theta_{out}$ in the equation, $\theta_{in}=\theta_{out}\pm\Delta\omega$, while maintaining $\theta_{in}$ at a constant value, or by scanning $\theta_{in}$ in the equation, $\theta_{in}=\theta_{out}\pm\Delta\omega$, while maintaining $\theta_{out}$ at a constant value.

To be more specific, the various parameters required to simulate the X-ray scattering curve are $R_0$, M, q, $\theta_{in}$, $\theta_{out}$, $\delta$, $\lambda$ and $\rho_0$, as may be seen from Equations (2) to (6). Of these parameters, $\underline{\delta}$ and $\rho_0$ are obtained from the reflectivity curve, q is obtained from $\theta_{in}$, $\theta_{out}$, $\delta$ and $\lambda$, and $R_0$ and $\underline{M}$ are fitting parameters. Thus, once the reflectivity curve is obtained, an X-ray scattering curve can be simulated easily and within a short time by calculating a scattering function.

After obtaining the simulated X-ray scattering curve, fitting is performed in Step S15 of FIG. 27 on the X-ray scattering curve thus simulated and the X-ray scattering curve actually obtained. In the fitting, the similarity of these curves, or the difference between them, is studied in Step S16. For example, the difference between these curves is given as follows:

$$X^2=\Sigma i(\log Ii(\exp)-\log Ii(\text{cal}))^2 \qquad (7)$$

where $I_i$ (exp) is the data actually obtained at ith measuring point, and $I_i$ (cal) is the data simulated at ith measuring point.

If the similarity or difference falls within a specific tolerance, the curves are regarded as coinciding with each other. Otherwise, they are regarded as not coinciding with each other. If the curves are regarded as not coinciding (i.e., if "NO" in Step S16), the control flow returns to Step S14. In Step S14, the fitting parameters [$R_0$, M], which indicate the coincidence with the X-ray scattering curve actually obtained, are changed. Also in Step S14, the X-ray scattering curve is simulated for the second time. Then, in Step S15, fitting is performed on the scattering curve newly simulated and the scattering curve actually obtained. Further, in Step S16, it is determined whether these curves coincide with each other. Steps S14 to S16 are repeated until the curves compared coincide with each other.

If these curves are determined to coincide (that is, if "YES" in Step S16), the values selected at this time for the fitting parameters represent the distribution that the particles assume in the sample being analyzed. More correctly, the value of "$R_0$" indicates the average size of the particles, and the value of "M" indicates the distribution broadening of the particles. In the fitting, optimal values for the fitting parameters can be efficiently obtained by means of, for example, the least-square method.

As described above, the X-ray scattering curve simulated is very similar to the X-ray scattering curve actually obtained, thanks to the use of a function that reflects the non-uniform density of the sample. In addition, the fitting parameters can represent the distribution of particle with high precision. It follows that the method of the invention can analyze, with high accuracy, thin films and bulk bodies for the distribution of the particles existing in them.

In this embodiment, only two items are measured of the sample, i.e., the reflectivity and the X-ray scattering curve. The sample can be analyzed within a short time, unlike in a conventional method such as gas-adsorption method. Further, thin films of any type can be analyzed, unlike in the gas-adsorption method that cannot analyze thin films into which the gas cannot be introduced. Moreover, a thin film to be analyzed need not be peeled from the substrate as in the small angle X-ray scattering method that is another conventional analysis method. Thus, the method according to the invention can analyze various thin films and various bulk bodies in non-destructive fashion and within a short time, for their non-uniformity of density.

In Equation (3), the slit function $W(q_N)$ is included in the scattering function. The slit function $W(q_N)$ may be, for example, a function of the type shown in FIG. 25. The slit function $W(q_N)$ can be obtained as has been explained with reference to FIG. 4 to FIG. 24. If an X-ray scattering curve is simulated by using a scattering function incorporating the slit function $W(q_N)$, as in the present embodiment, fitting parameters "$R_0$" and "M" will be acquired, which have highly reliable and accurate values that compensate for the umbrella effect of the slits used in the optical system.

The sample-analyzing apparatuses 1 and 31, which are shown in FIGS. 1 and 26, respectively, shall be compared in terms of structure. A data-processing means identical to the means 16 shown in FIG. 1 is incorporated in the X-ray measuring device 32 shown in FIG. 26. A slit-function output means and a model-function output means, which are identical to the means 17 and 18 shown in FIG. 1, respectively, are incorporated in, or connected to, the function-storing means 42 shown in FIG. 26. An $I_{calc}$-calculating means identical to the means 19 shown in FIG. 1 is incorporated in the simulation means 43 shown in FIG. 26. A comparing means identical to the means 21 shown in FIG. 1 is incorporated in the fitting means 44 shown in FIG. 26.

(Other Embodiments)

The present invention has been described, with reference to the preferred embodiments. Nevertheless, the invention is not limited to the embodiments described above. Various changes and modifications can be made within the scope and spirit of the invention as defined in the claims that will be described hereinafter.

In the embodiments described above, the propagation rays are X-rays. Nonetheless, the X-rays may be replaced by particle beams such as neutron beams or electron beams. In this case, the scattering function of Equation (3) can be applied to obtain the reflectivity function and scattering curve of the particle beams, without being modified at all. The scattering function thus obtained may be used to perform the analysis of FIG. 27. Then, the density non-uniformity of the sample can be analyzed with high precision, if fitting parameters are applied to the fitting of the particle-beam scattering curve simulated and the particle-beam scattering curve actually obtained.

What is claimed is:

1. A sample-analyzing method comprising:
providing an incident beam slit between a propagation-ray source and a sample;
providing a receiving side beam slit between said sample and detecting means;
causing said detecting means to detect propagation rays re-generated from said sample and coming through said receiving side beam slit when said sample is irradiated with said propagation rays applied through said incident beam slit;
measuring a value from a value detected by the detecting means; and
calculating a true value from said value measured, by using a slit function representing an influence which said incident beam slit and said receiving side beam slit impose on said value detected by said detecting means,
wherein said slit function is determined from an intensity distribution of said propagation rays scattered again from said sample, and
said slit function is further determined from X-ray irradiating positions in a lengthwise direction of said sample.

2. The sample-analyzing method according to claim 1, wherein said propagation rays are X-rays or particle beams, and said particle beams are neutron beams or electron beams.

3. The sample-analyzing method according to claim 2, wherein said slit function is determined from a variable that is the position in a lengthwise direction of said sample, where said sample is irradiated with said propagation rays.

4. The sample-analyzing method according to claim 2, wherein said slit function is determined based on the fact that an angle formed by lines of sight which extends from said sample to said propagation-ray source through said incident beam slit and an angle formed by lines of sight which extends from said sample to said detecting means through said receiving side beam slit change in accordance with a position in a lengthwise direction of said sample.

5. The sample-analyzing method according to claim 2, wherein said slit function is determined from a convolution of two intensity distributions that said propagation rays assume at an incident side and receiving side of said sample, respectively.

6. The sample-analyzing method according to claim 1, wherein said slit function is determined from a variable that represents a position in a lengthwise direction of said sample, where said sample is irradiated with the propagation rays.

7. The sample-analyzing method according to claim 6, wherein said slit function is determined based on the fact that an angle formed by lines of sight which extends from said sample to said propagation-ray source through said incident beam slit and an angle formed by lines of sight which extends from said sample to said detecting means through said receiving side beam slit change in accordance with a position in a lengthwise direction of said sample.

8. The sample-analyzing method according to claim 6, wherein said slit function is determined from a convolution of two intensity distributions that said propagation rays assume at an incident side and receiving side of said sample, respectively.

9. The sample-analyzing method according to claim 1, wherein said slit function is determined based on the fact that an angle formed by lines of sight which extends from said sample to said propagation-ray source through said incident beam slit and an angle formed by lines of sight which extends from said sample to said detecting means through said receiving side beam slit change in accordance with a position in a lengthwise direction of said sample.

10. The sample-analyzing method according to claim 9, wherein said slit function is determined from a convolution of two intensity distributions that said propagation rays assume at an incident side and receiving side of said sample, respectively.

11. The sample-analyzing method according to claim 1, wherein said slit function is determined from a convolution of two intensity distributions that said propagation rays assume at an incident side and receiving side of said sample, respectively.

12. A sample-analyzing apparatus comprising:
a propagation-ray source for emitting propagation rays that irradiate a sample;
an incident beam slit provided between said propagation-ray source and said sample;
detecting means for detecting propagation rays scattered again from said sample;
a receiving side beam slit provided between said sample and said detecting means;
slit-function outputting means for calculating and outputting a slit function from geometrical conditions input;
model-function outputting means for outputting a model function containing fitting parameters for use in calculating an X-ray scattering intensity model;
function-calculating means for calculating an analysis function from said slit function and said model function; and
parameter-optimizing means for determining a similarity between said analysis function calculated and a function actually measured, and for optimizing said fitting parameters contained in said model function, thereby to enhance the similarity between said analysis function calculated and said function actually measured;
wherein said slit-function outputting means determines said slit function based on an intensity distribution of said propagation rays scattered again from said sample and x-ray irradiating positions in a lengthwise direction of said sample.

13. The sample-analyzing apparatus according to claim 12, wherein said propagation rays are X-rays or particle beams, and the particle beams are neutron beams or electron beams.

14. The sample-analyzing apparatus according to claim 12, wherein said slit function is determined from a variable that represents a position in a lengthwise direction of said sample, where said sample is irradiated with said propagation rays.

15. The sample-analyzing apparatus according to claim 12, wherein said slit function is determined based on the fact that an angle formed by lines of sight which extends from said sample to said propagation-ray source through said incident beam slit and an angle formed by lines of sight which extends from said sample to said detecting means through said receiving side beam slit change in accordance with a position in a lengthwise direction of said sample.

16. The sample-analyzing apparatus according to claim 12, wherein said slit function is determined from a convolution of two intensity distributions that said propagation rays assume at an incident side and receiving side of said sample, respectively.

17. A sample-analyzing apparatus comprising:
a propagation-ray source for emitting propagation rays that irradiate a sample;
an incident beam slit provided between said propagation-ray source and said sample;
detecting means for detecting propagation rays scattered again from said sample;
a receiving side beam slit provided between said sample and said detecting means;
slit-function outputting means for calculating and outputting a slit function from geometrical conditions pertaining to said incident beam slit and receiving side beam slit;
model-function outputting means for outputting a model function containing fitting parameters for use in calculating an X-ray scattering intensity model;
function-calculating means for calculating an analysis function from said slit function and said model function; and
parameter-optimizing means for determining a similarity between said analysis function calculated and a function actually measured, and for optimizing said fitting parameters contained in said model function, thereby to enhance the similarity between said analysis function calculated and said function actually measured;
wherein said slit-function outputting means determines said slit function based on an intensity distribution of said propagation rays scattered again from said sample and x-ray irradiating positions in a lengthwise direction of said sample.

18. The sample-analyzing apparatus according to claim 17, wherein said propagation rays are X-rays or particle beams, and said particle beams are neutron beams or electron beams.

19. The sample-analyzing apparatus according to claim 17, wherein said slit function is determined from a variable that represents a position in a lengthwise direction of said sample, where said sample is irradiated with said propagation rays.

20. The sample-analyzing apparatus according to claim 17, wherein said slit function is determined based on the fact that an angle formed by lines of sight which extends from said sample to said propagation-ray source through said incident beam slit and an angle formed by lines of sight which extends from said sample to said detecting means through said receiving side beam slit change in accordance with a position in a lengthwise direction of said sample.

21. The sample-analyzing apparatus according to claim 17, wherein side slit function is determined from a convolution of two intensity distributions that said propagation rays assume at an incident side and receiving side of said sample, respectively.

* * * * *